US011046676B2

(12) United States Patent
Vasireddi et al.

(10) Patent No.: US 11,046,676 B2
(45) Date of Patent: Jun. 29, 2021

(54) PROCESS FOR PREPARATION OF EMPAGLIFLOZIN OR ITS CO-CRYSTALS, SOLVATES AND THEIR POLYMORPHS THEREOF

(71) Applicant: Laurus Labs Limited, Hyderabad (IN)

(72) Inventors: Uma Maheswar Rao Vasireddi, Hyderabad (IN); Sanjay Kumar Dehury, Hyderabad (IN); Nagaraju Mekala, Hyderabad (IN); Jahangeer Baba Shaik, Hyderabad (IN); Srinivas Lagadapati, Hyderabad (IN)

(73) Assignee: Laurus Labs Limited, Hyderabad (IN)

( * ) Notice: Subject to any disclaimer, the term of this patent is extended or adjusted under 35 U.S.C. 154(b) by 0 days.

(21) Appl. No.: 16/619,831

(22) PCT Filed: Jun. 5, 2018

(86) PCT No.: PCT/IB2018/054013
§ 371 (c)(1),
(2) Date: Dec. 5, 2019

(87) PCT Pub. No.: WO2018/224957
PCT Pub. Date: Dec. 13, 2018

(65) Prior Publication Data
US 2020/0131163 A1    Apr. 30, 2020

(30) Foreign Application Priority Data
Jun. 5, 2017 (IN) .............................. 201741019614

(51) Int. Cl.
*C07D 407/12*    (2006.01)

(52) U.S. Cl.
CPC ........ *C07D 407/12* (2013.01); *C07B 2200/13* (2013.01)

(58) Field of Classification Search
CPC ................ C07D 407/12; C07D 407/10; C07B 2200/13; C07F 7/1804
USPC ........................................................ 549/415
See application file for complete search history.

(56) References Cited

U.S. PATENT DOCUMENTS

| 7,579,449 | B2 | 8/2009 | Eckhardt et al. |
| 7,772,191 | B2 | 8/2010 | Eckhardt et al. |
| 9,024,010 | B2 | 5/2015 | Weber et al. |
| 2016/0318965 | A1 | 11/2016 | Kumar et al. |

OTHER PUBLICATIONS

Matt Hrapchak et al., "Synthesis of empagliflozin, a novel and selective sodium-glucose co-transporter-2 inhibitor labeled with carbon-14 and carbon-13" J. Label Compd. Radiopharm 2014, 57 687-694 & Oct. 21, 2014 Scheme 1-3.

Xiao-Jun Wang et al., "Efficient Synthesis of Empagliflozin, an Inhibitor of SGLT-2, Utilizing an AIC13Promoted Silane Reduction of a Glycopyranoside" Org. Lett. 2014, 16, 40904093 & Jul. 25, 2014 Scheme 1-3 & Table 1-2.

*Primary Examiner* — Taylor V Oh
(74) *Attorney, Agent, or Firm* — Blank Rome LLP

(57) ABSTRACT

The present invention relates to process for the preparation of Empagliflozin or its co-crystals, solvates and/or polymorphs thereof. The present invention also relates to novel intermediates used therein, and process for the preparation thereof. The present invention further relates to process for preparation of amorphous and crystalline form of Empagliflozin.

49 Claims, 4 Drawing Sheets

PROCESS FOR PREPARATION OF EMPAGLIFLOZIN OR ITS CO-CRYSTALS, SOLVATES AND THEIR POLYMORPHS THEREOF

CROSS-REFERENCE TO RELATED APPLICATIONS

This application is a national stage application of and claims the benefit of International Application PCT/IB2018/054013, filed on Jun. 5, 2018, which is based on and claims the benefit of the filing date of Indian Provisional Application No. 201741019614, filed on Jun. 5, 2017, entitled "Novel process for preparation of empagliflozin or its co-crystals, solvates and their polymorphs thereof", the contents of which are incorporated by reference herein.

FIELD OF THE INVENTION

The present invention relates to process for the preparation of Empagliflozin or its co-crystals, solvates and/or polymorphs thereof. The present invention also encompasses novel intermediates used therein. The present invention further relates to process for preparation of amorphous and crystalline form of Empagliflozin.

BACKGROUND OF THE INVENTION

Empagliflozin is one of the antidiabetic agent from the group of sodium glucose co-transporter 2 (SGLT2) inhibitors for the treatment of type 2 diabetes mellitus. Empagliflozin is chemically known as (1S)-1, 5-anhydro-1-(4-chloro-3-{4-[(3S)-tetrahydrofuran-3-yloxy]benzyl}phenyl)-D-glucitol and has the following structure of Formula I:

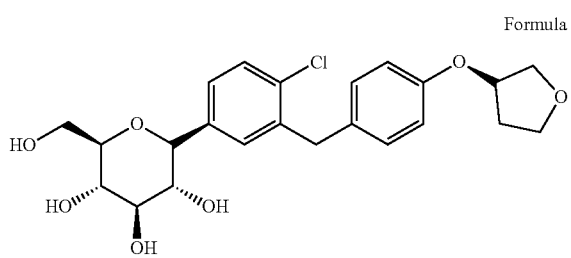

Formula I

Empagliflozin is formulated as an immediate-release tablet for once-daily oral administration at a recommended dose of 25 mg as an adjunct to diet and exercise to improve glycaemic control in adults with type 2 diabetes mellitus either as mono-therapy or as an add-on with other oral antidiabetic treatments or insulin.

Empagliflozin and a process for its preparation thereof, was first described under U.S. Pat. No. 7,579,449 ("the '449 patent") and the disclosed process of empagliflozin is schematically represented as follows:

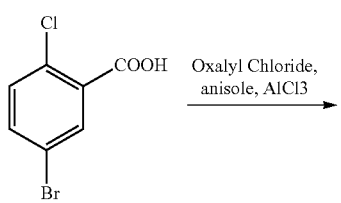

5-Bromo-2-chloro-benzoic acid

Oxalyl Chloride, anisole, AlCl3

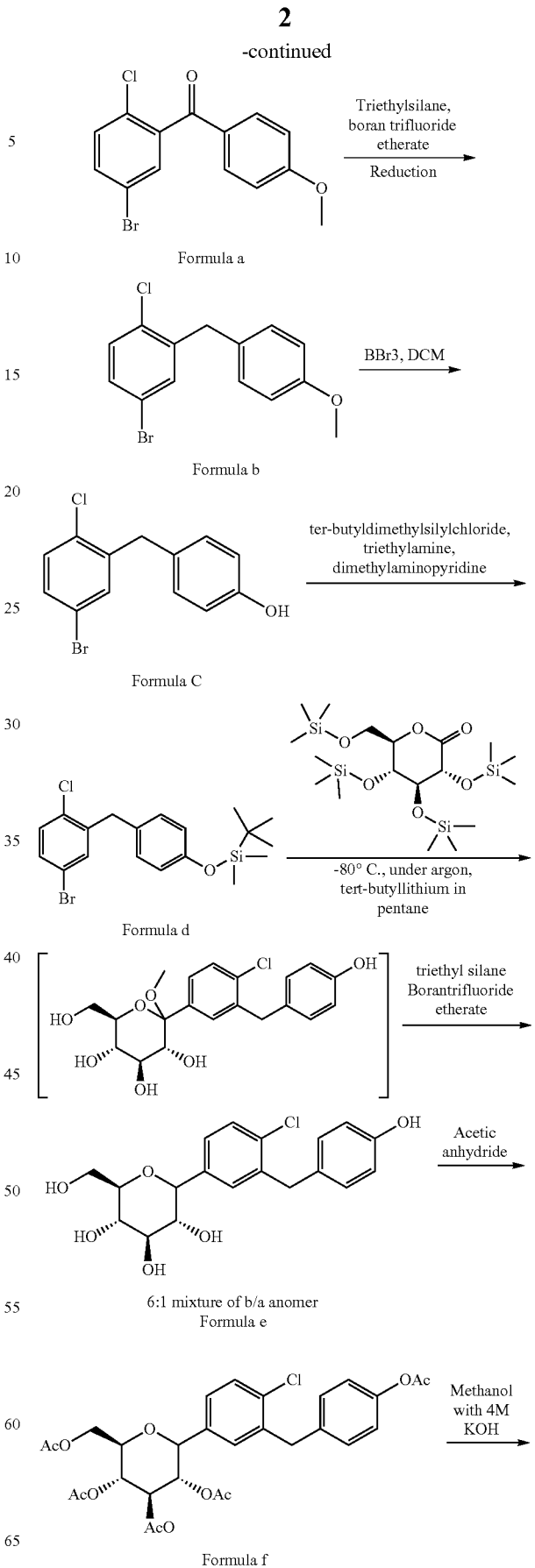

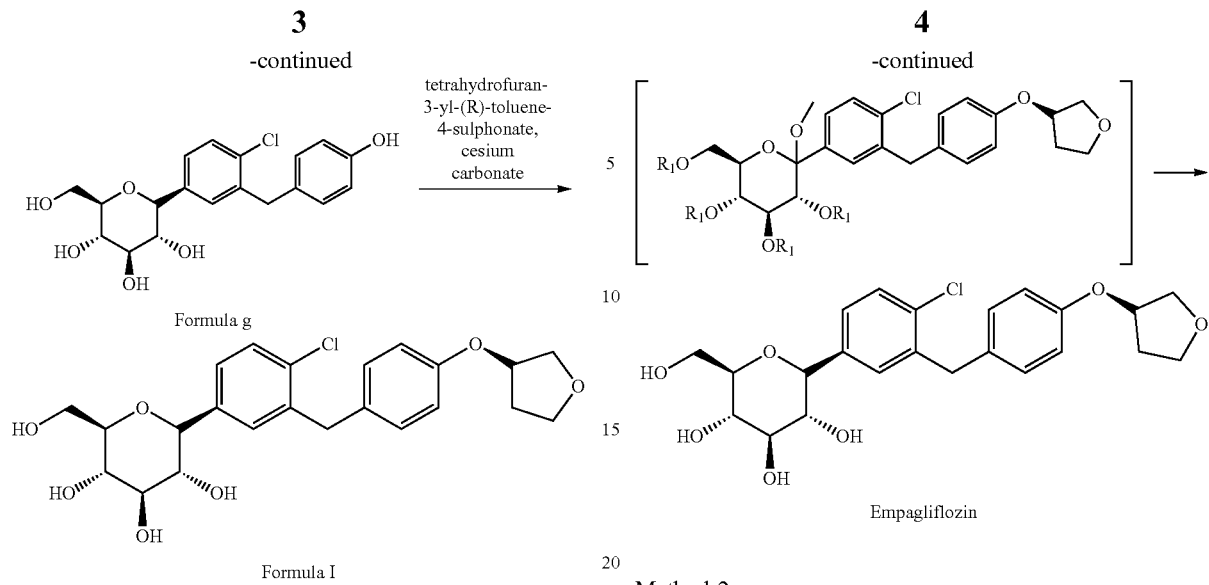

Empagliflozin process disclosed under the '449 patent has certain drawbacks, which are as follows:
a) extensive chromatography purification steps are involved to isolate the intermediate compound of Formula (d) and Formula (e) and the final compound,
b) intermediate of Formula (e) obtained as a 6:1 mixture of β/α anomer, which process requires additional purification steps such as formation of acetyl derivative followed by neutralization of the same to get pure β-anomer, and
c) isolation of the final empagliflozin by chromatography using dichloromethane/methanol and fails to characterize the final API.

U.S. Pat. No. 7,772,191 ("the '191 patent") discloses processes for preparation of Empagliflozin through intermediate of 4-(iodo/bromo)-1-chloro-2-(4-tetrahydrofuran-3-yloxy-benzyl)-benzene. The processes disclosed in the '191 patent are schematically represented as follows:

Method-1:

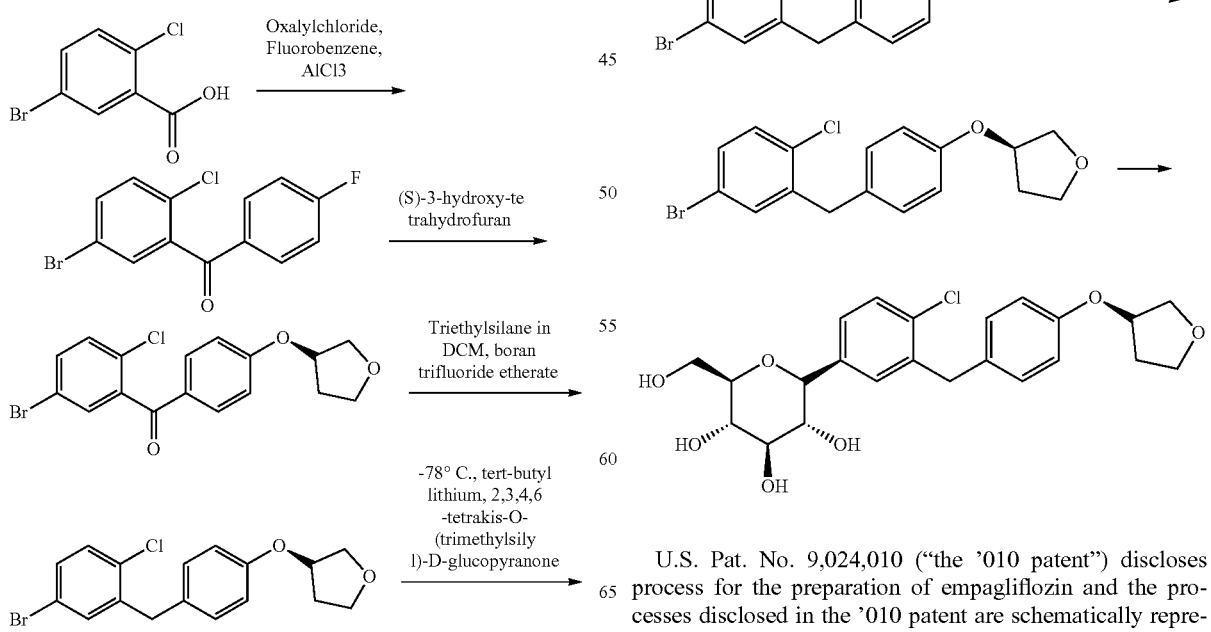

U.S. Pat. No. 9,024,010 ("the '010 patent") discloses process for the preparation of empagliflozin and the processes disclosed in the '010 patent are schematically represented as follows:

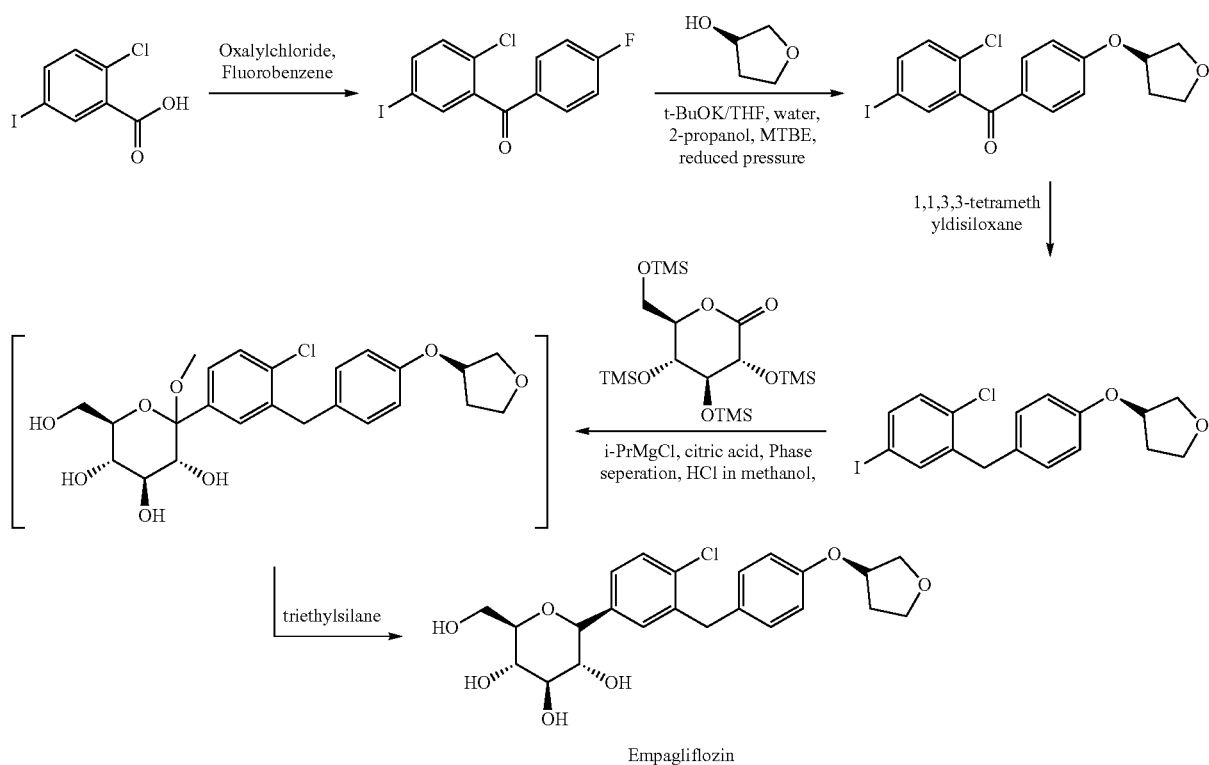
U.S. Pat. Appl. No. 2016318965 ("the 965 patent application") discloses method of preparation of empagliflozin through novel intermediates thereof. The processes disclosed in the '965 patent application is schematically represented as follows:
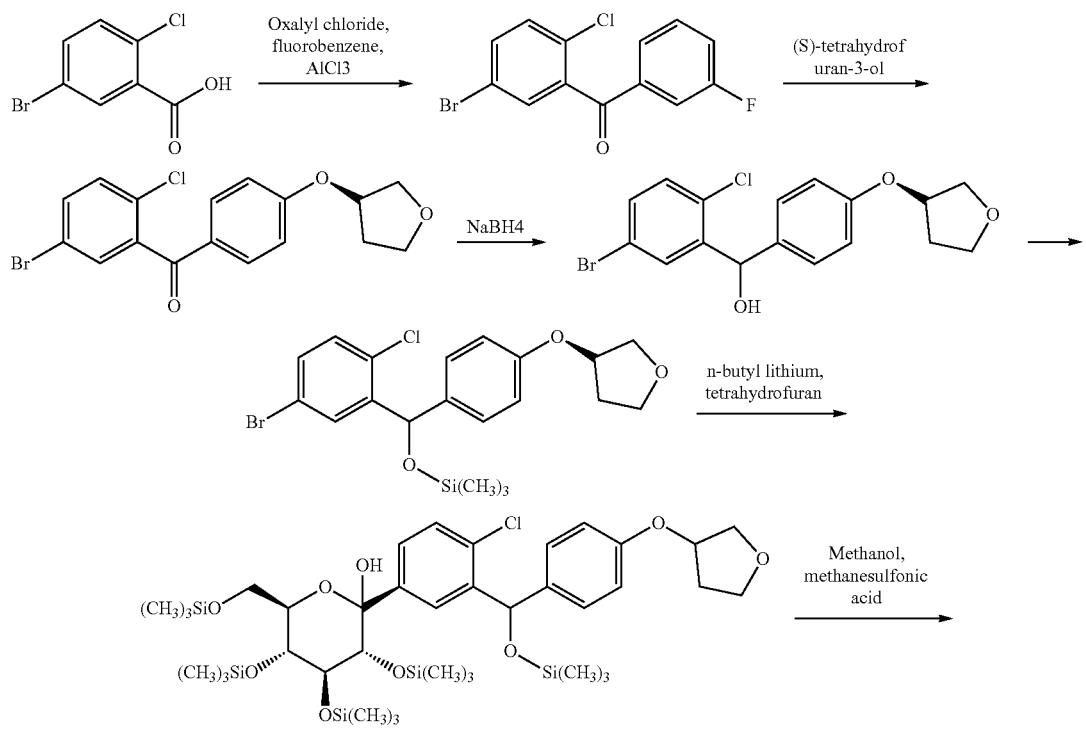

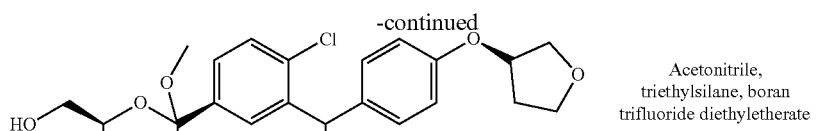

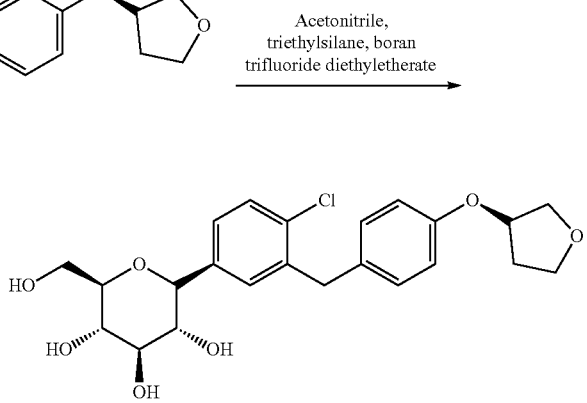

Because of intrinsic fragility of empagliflozin, due to its high chirality, empagliflozin obtained from the above processes was not satisfactory from purity point of view. Empagliflozin synthetic procedures as described in the art contained relatively large amounts of impurities. Extensive purification procedures are required in order to limit the impurities to less than the required as per regulatory guidelines.

The process for preparation of empagliflozin, described in the above literature(s) involves isolation of pure intermediates by chromatography purification, which is expensive and difficult to implement in the large scale.

Due to potentially high commercial importance, there is a need in the industry for development of an efficient process to prepare empagliflozin, which is cost effective, industrially viable, and provide empagliflozin substantially free of impurities, avoiding usage of chromatographic purifications and avoiding usage of Grignard reagents.

Accordingly, the present invention provides a novel process for preparation of empagliflozin, or its co-crystals, solvates and/or their polymorphs thereof, through novel intermediates.

SUMMARY OF THE INVENTION

The present invention provides a process for the preparation of empagliflozin of Formula I or its co-crystals, solvates and/or their polymorphs thereof by using novel intermediates.

In an aspect, the present invention provides a process for the preparation of empagliflozin of Formula I or its co-crystals, solvates and/or their polymorphs thereof;
comprising:

Formula I

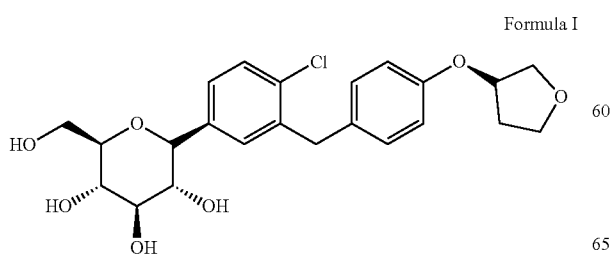

a) reacting an aldehyde compound of Formula IX with a compound of Formula VIII or reactive derivative thereof, to obtain a compound of formula VII or a reactive derivative thereof;

Formula VIII

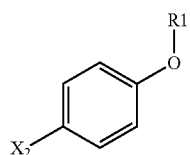

Formula IX

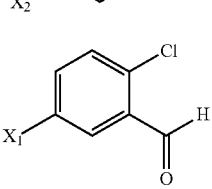

Formula VII

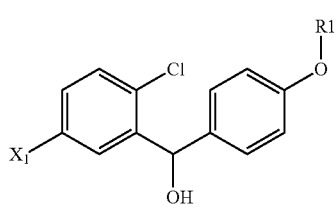

wherein "$X_1$" and "$X_2$" independently represents a suitable leaving group and $R_1$ represents hydrogen or a suitable hydroxyl protecting group;

b) optionally protecting the hydroxyl group of compound of Formula VII to obtain a compound of Formula VI; wherein $R_1$ and $R_2$ independently represents hydrogen or a suitable hydroxyl protecting group;

Formula VII

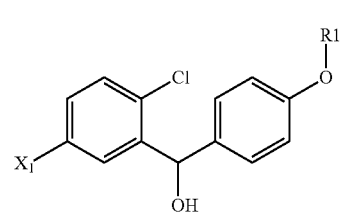

Formula VI

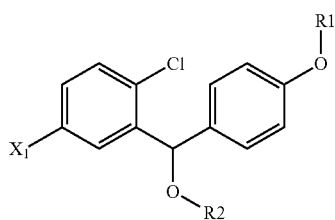

c) condensing the compound of Formula VII or its protected derivative of Formula VI with glucono lactone of compound of Formula V to obtain a compound of formula IV"; wherein $R_1$, $R_2$, $P_1$, $P_2$, $P_3$, and $P_4$ independently represents hydrogen or a suitable hydroxyl protecting group;

Formula V

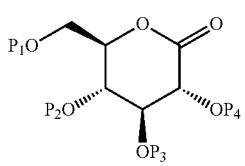

Formula IV"

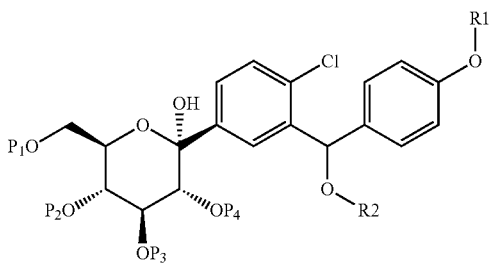

d) converting the compound of Formula IV" to a compound of Formula IV; wherein $R_3$ represents an alkyl group;

Formula IV

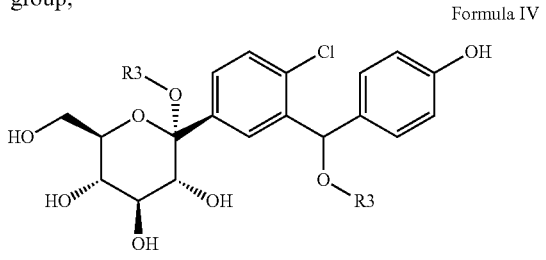

e) reducing the compound of Formula IV in to a compound of Formula III; and

Formula III

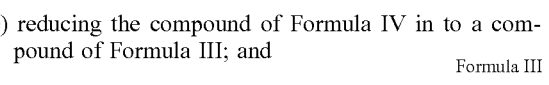

f) reacting the compound of Formula III with a compound of Formula II to obtain empagliflozin of Formula I;

Formula II

Formula I

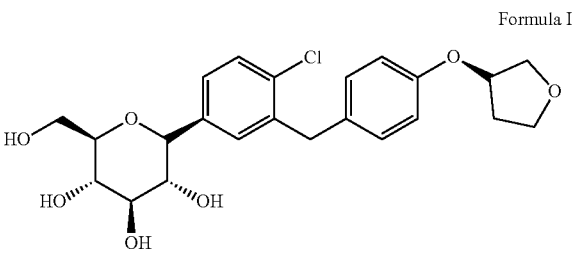

wherein "Q" represents a suitable leaving group.

In another aspect, the present invention provides a process for the preparation of empagliflozin of Formula I or its co-crystals, solvates and/or their polymorphs thereof, comprising:

a) reacting a compound of Formula IV" with a suitable acid to obtain a compound of Formula IV-1; wherein $R_1$, $R_2$, $P_1$, $P_2$, $P_3$, and $P_4$ independently represents hydrogen or a suitable hydroxyl protecting group;

Formula IV"

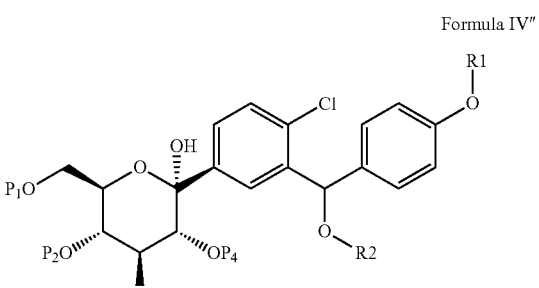

Formula IV-1

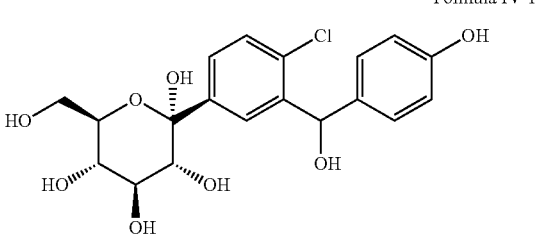

b) treating the compound of Formula IV-I with an alcohol to obtain a compound of Formula IV, wherein $R_3$ represents an alkyl group;

Formula IV

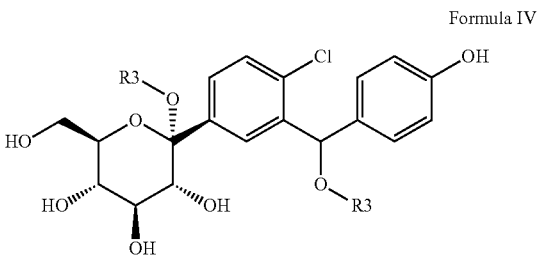

c) reducing the compound of Formula IV in to a compound of Formula III; and

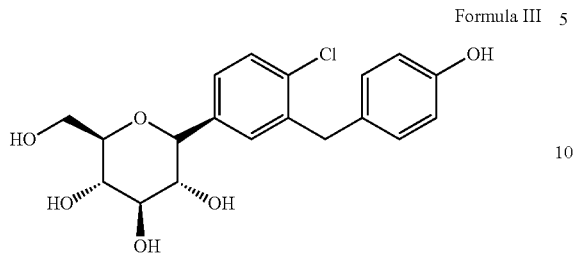

Formula III d) reacting the compound of Formula III with a compound of Formula II to obtain empagliflozin of Formula I:

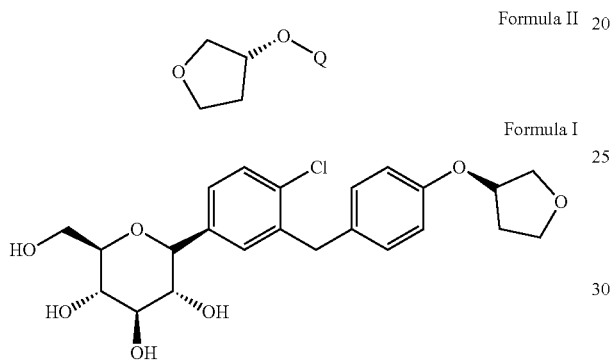

Formula II

Formula I wherein "Q" represents a suitable leaving group.

In another aspect, the present invention provides a process for the preparation of empagliflozin of Formula I or its co-crystals, solvates and/or their polymorphs thereof, comprising:
a) protecting hydroxyl group of a compound of Formula VII with a suitable hydroxyl protecting compound to obtain a compound of Formula VI; wherein $R_1$ and $R_2$ independently represents hydrogen or a suitable hydroxyl protecting group;
b) condensing the compound of Formula VII or its protected derivative of Formula VI with glucono lactone of compound of Formula V to obtain a compound of Formula IV'''; wherein $R_1$, $R_2$, $P_1$, $P_2$, $P_3$, and $P_4$ independently represents hydrogen or a suitable hydroxyl protecting group;
c) converting the compound of Formula IV'' to a compound of Formula IV; wherein R3 represents an alkyl group;
d) reducing the compound of Formula IV in to a compound of Formula III; and
e) reacting the compound of Formula III with a compound of Formula II to obtain empagliflozin of Formula I; wherein "Q" represents a suitable leaving group.

In another aspect, the present invention provides a process for the preparation of empagliflozin of Formula I or its co-crystals, solvates and/or their polymorphs thereof, comprising:
a) condensing a compound of Formula VII or its protected derivative of Formula VI with glucono lactone of compound of Formula V to obtain a compound of Formula IV'''; wherein $R_1$, $R_2$, $P_1$, $P_2$, $P_3$, and $P_4$ independently represents hydrogen or a suitable hydroxyl protecting group;
b) converting the compound of Formula IV'' to a compound of Formula IV; wherein R3 represents an alkyl group;
c) reducing the compound of Formula IV in to a compound of Formula III; and
d) reacting the compound of Formula III with a compound of Formula II to obtain empagliflozin of Formula I; wherein "Q" represents a suitable leaving group.

In another aspect, the present invention provides a process for the preparation of empagliflozin of Formula I or its co-crystals, solvates and/or their polymorphs thereof, comprising:
a) converting a compound of Formula IV'' to a compound of Formula IV; wherein R3 represents an alkyl group;
b) reducing the compound of Formula IV in to a compound of Formula III; and
c) reacting the compound of Formula III with a compound of Formula II to obtain empagliflozin of Formula I; wherein "Q" represents a suitable leaving group.

In another aspect, the present invention provides a process for the preparation of empagliflozin of Formula I or its co-crystals, solvates and/or their polymorphs thereof, comprising:
a) reducing a compound of Formula IV with a suitable reducing agent to obtain a compound of Formula III; and
b) reacting the compound of Formula III with a compound of Formula II to obtain empagliflozin of Formula I; wherein "Q" represents a suitable leaving group.

In another aspect, the present invention provides a process for the preparation of empagliflozin of Formula I or its co-crystals, solvates and/or their polymorphs thereof, comprising:
a) reducing a compound of Formula IV-I with a suitable reducing agent to obtain a compound of Formula III; and
b) reacting the compound of Formula III with a compound of Formula II to obtain empagliflozin of Formula I; wherein "Q" represents a suitable leaving group.

In another aspect, the present invention provides a process for the preparation of empagliflozin of Formula I or its co-crystals, solvates and/or their polymorphs thereof, comprising:
a) reacting an aldehyde compound of Formula IX with a compound of Formula VIII or reactive derivative thereof, to obtain a compound of Formula VII or a reactive derivative thereof; wherein "$X_1$" and "$X_2$" independently represents a suitable leaving group and $R_1$ represents hydrogen or a suitable hydroxyl protecting group; and
b) converting the compound of Formula VII in to empagliflozin of Formula I.

In another aspect, the present invention provides a process for the preparation of empagliflozin of Formula I or its co-crystals, solvates and/or their polymorphs thereof; comprising:
a) reacting an aldehyde compound of Formula IX with a compound of Formula VIII or reactive derivative thereof, to obtain a compound of Formula VII or a reactive derivative thereof; wherein "$X_1$" and "$X_2$" independently represents a suitable leaving group and $R_1$ represents hydrogen or a suitable hydroxyl protecting group,
b) protecting the hydroxyl group of compound of Formula VII with a suitable hydroxyl protecting compound to obtain a compound of Formula VI; wherein $R_1$ and $R_2$ independently represents hydrogen or a suitable hydroxyl protecting group; and
c) converting the compound of Formula VI in to empagliflozin of Formula I.

In another aspect, the present invention provides a process for the preparation of empagliflozin of Formula I or its co-crystals, solvates and/or their polymorphs thereof, comprising:
a) condensing a compound of Formula VII or its protected derivative of Formula VI with glucono lactone of compound of Formula V to obtain a compound of Formula IV"; wherein R₁, R₂, P₁, P₂, P₃, and P₄ independently represents hydrogen or a suitable hydroxyl protecting group; and
b) converting the compound of Formula VI" in to empagliflozin of Formula I.

In another aspect, the present invention provides a process for the preparation of empagliflozin of Formula I or its co-crystals, solvates and/or their polymorphs thereof, comprising:
a) condensing a compound of Formula VII or its protected derivative of Formula VI with glucono lactone of compound of Formula V to obtain a compound of Formula IV"; wherein R₁, R₂, P₁, P₂, P₃, and P₄ independently represents hydrogen or a suitable hydroxyl protecting group;
b) reacting a compound of Formula IV" with a suitable acid in an alcohol to obtain a compound of Formula IV, wherein R₃ represents an alkyl group; and
c) converting the compound of Formula VI in to empagliflozin of Formula I.

In another aspect, the present invention provides a process for the preparation of empagliflozin of Formula I or its co-crystals, solvates and/or their polymorphs thereof, comprising: reducing a compound of Formula IV with a suitable reducing agent to obtain a compound of Formula III; and converting the compound of Formula III in to empagliflozin of Formula I.

In another aspect, the present invention provides a compound of Formula VII

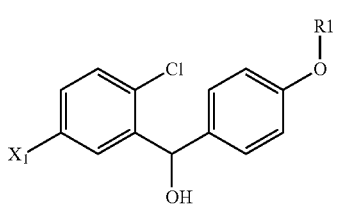

Formula VII wherein "X₁" represents a suitable leaving group and R₁ represents hydrogen or a suitable hydroxyl protecting group.

In another aspect, the present invention provides a compound of Formula VII

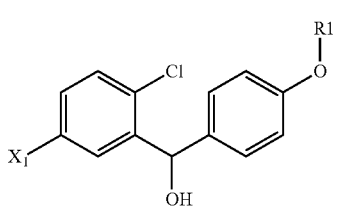

Formula VII wherein X₁ represents a suitable leaving group, which is selected from the group consisting of chloro, bromo, iodo, methane sulfonyloxy, p-toluenesulphonyloxy or perfluoroalkylsulfonate; and R₁ represents hydrogen or a suitable hydroxyl protecting group which includes but is not limited to alkyl, acetyl, pivaloyl, methoxymethyl, benzyl, benzoyl, tert-butoxycarbonyl, benzyloxycarbonyl, tetrahydropyranyl, trimethylsilyl, triethylsilyl, t-butyl(dimethyl)silyl, t-butyl (diphenyl)silyl, tri(isopropyl)silyl, 2-(trimethylsilyloxy) ethyl, tert-Butyl 2,2,2-trichloroacetimidate, 4-Methoxybenzyl-2,2,2-trichloroacetimidate, Benzyl 2,2,2-trichloroacetimidate, Methyl 2,2,2-trichloroacetimidate and O-Allyl 2,2,2-trichloroacetimidate and the like.

In another aspect, the present invention provides a compound of Formula VII

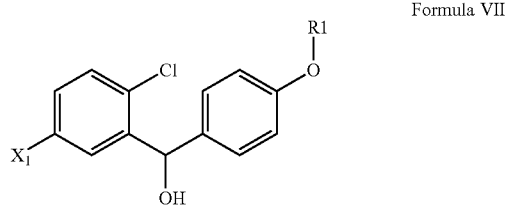

Formula VII wherein the X₁ is bromo and the R₁ is t-butyl(dimethyl)silyl.

In another aspect, the present invention provides a compound of Formula VI

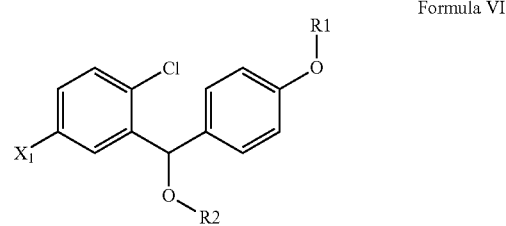

Formula VI wherein "X₁" represents a suitable leaving group and R₁ and R₂ independently represents hydrogen or a suitable hydroxyl protecting group.

In another aspect, the present invention provides a compound of Formula VI

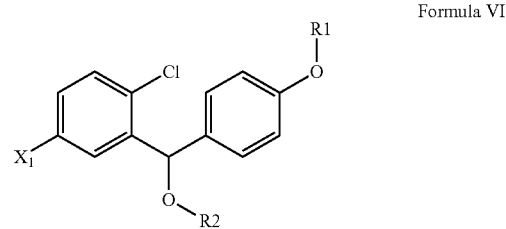

Formula VI wherein X₁ represents a suitable leaving group, which is selected from the group consisting of chloro, bromo, iodo, methane sulfonyloxy, p-toluenesulphonyloxy or perfluoroalkylsulfonate; and R₁ and R₂ independently represents hydrogen or a suitable hydroxyl protecting group which includes but is not limited to alkyl, acetyl, pivaloyl, methoxymethyl, benzyl, benzoyl, tert-butoxycarbonyl, benzyloxycarbonyl, tetrahydropyranyl, trimethylsilyl, triethylsilyl, t-butyl(dimethyl)silyl, t-butyl(diphenyl)silyl, tri(isopropyl)silyl, 2-(trimethylsilyloxy)ethyl, tert-Butyl 2,2,2-trichloroacetimidate, 4-Methoxybenzyl-2,2,2-trichloroacetimidate, Benzyl 2,2,2-trichloroacetimidate, Methyl 2,2,2-trichloroacetimidate and O-Allyl 2,2,2-trichloroacetimidate and the like.

In another aspect, the present invention provides a compound of Formula VI

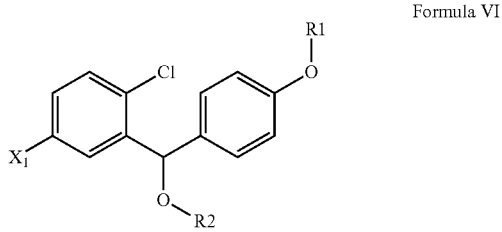

Formula VI wherein the $X_1$ is bromo and the $R_1$ is t-butyl(dimethyl)silyl and $R_2$ is trimethylsilyl In another aspect, the present invention provides a compound of Formula IV"

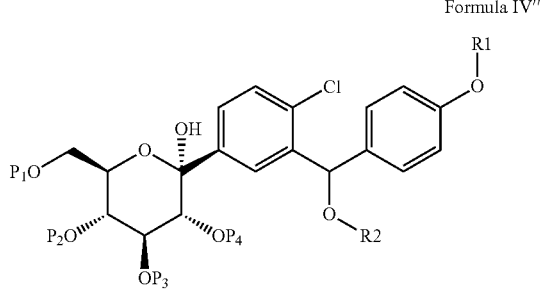

Formula IV"

wherein $R_1$, $R_2$, P, $P_1$, $P_2$, $P_3$ and $P_4$ independently represents hydrogen or a suitable hydroxyl protecting group.

In another aspect, the present invention provides a compound of Formula IV"

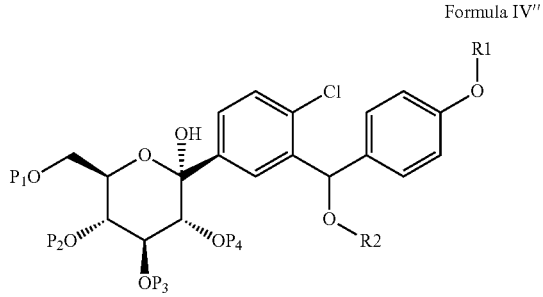

Formula IV"

wherein $R_1$ and $R_2$ independently represents hydrogen or a suitable hydroxyl protecting group which includes but is not limited to alkyl, acetyl, pivaloyl, methoxymethyl, benzyl, benzoyl, tert-butoxycarbonyl, benzyloxycarbonyl, tetrahydropyranyl, trimethylsilyl, triethylsilyl, t-butyl(dimethyl)silyl, t-butyl(diphenyl)silyl, tri(isopropyl)silyl, 2-(trimethylsilyloxy)ethyl, tert-Butyl 2,2,2-trichloroacetimidate, 4-Methoxybenzyl-2,2,2-trichloroacetimidate, Benzyl 2,2,2-trichloroacetimidate, methyl 2,2,2-trichloroacetimidate and O-allyl 2,2,2-trichloroacetimidate and the like; wherein P, $P_1$, $P_2$, $P_3$ and $P_4$ independently represents hydrogen or a suitable hydroxyl protecting group, wherein the hydroxyl protecting groups are selected from the group consisting of alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like. Further, the protecting groups for hydroxyl groups may form acetal or silyl acetal together with adjacent hydroxyl groups.

In another aspect, the present invention provides a compound of Formula IV"

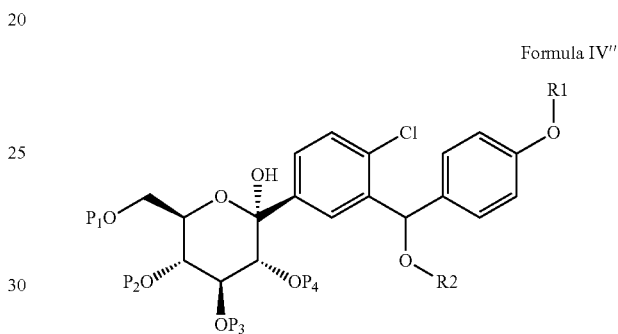

Formula IV"

wherein the $R_1$ is t-butyl(dimethyl)silyl, $R_2$ is trimethylsilyl and each of P, $P_1$, $P_2$, $P_3$ and $P_4$ is trimethylsilyl.

In another aspect, the present invention provides a compound of Formula IV-I

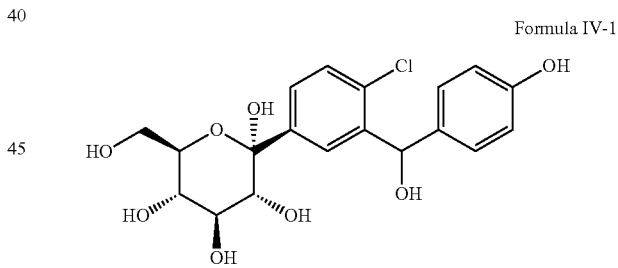

Formula IV-1

In another aspect, the present invention provides a compound of Formula IV

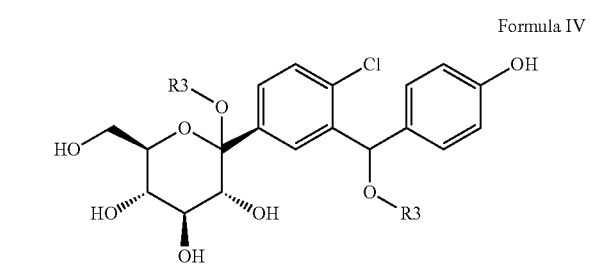

Formula IV wherein $R_3$ represents an alkyl group.

In another aspect, the present invention provides a compound of Formula IV, wherein $R_3$ represents a $C_{1-12}$ alkyl group.

In another aspect, the present invention provides a compound of Formula IV, wherein $R_3$ represents methyl.

In accordance with another embodiment, the present invention provides a process for the preparation of empagliflozin using one or more of the novel intermediates of Formula VII, Formula VI, Formula IV, Formula IV'' or Formula IV.

In another aspect, the present invention further provides pure compound of formula II, comprising:

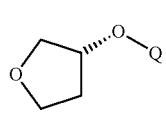

Formula II a) providing a solution comprising compound of Formula II in an organic solvent,
b) cooling the solution to precipitation, and
c) isolating the pure compound of Formula II In another aspect, the present invention provides a process for the preparation of empagliflozin of Formula I or its co-crystals, solvates and/or their polymorphs thereof, comprising:
a) providing a solution comprising compound of Formula II in organic solvent
b) cooling the solution to precipitation,
c) isolating the pure compound of Formula II, and
d) converting the pure compound of Formula II into empagliflozin or its co-crystals, solvates and/or their polymorphs thereof.

In another aspect, the present invention provides a process for the preparation of empagliflozin of Formula I or its co-crystals, solvates and/or their polymorphs thereof;

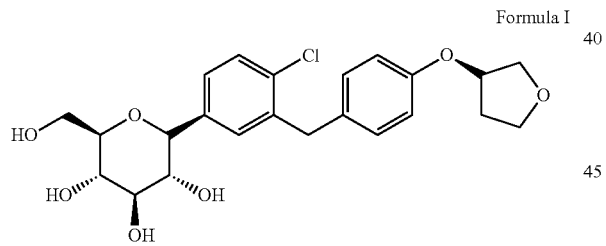

Formula I comprising:
a) reacting a compound of Formula IXa with a compound of Formula VIIIa to obtain a compound of Formula VIIa;

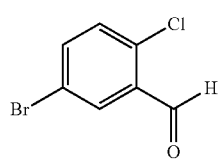

Formula IXa

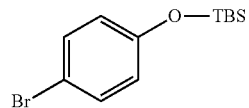

Formula VIIIa

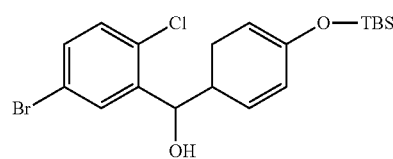

Formula VIIa b) converting the compound of Formula VIIa to compound of Formula VIa

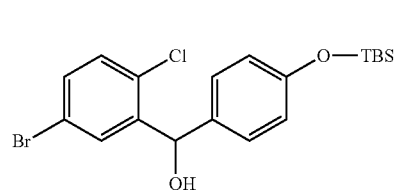

Formula VIIa

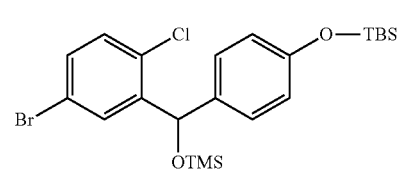

Formula VIa c) condensing the compound of Formula VIa with glucono lactone of compound of Formula Va to obtain compound of formula IV''a

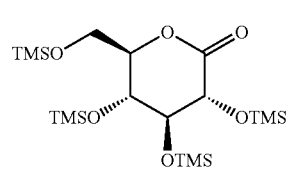

Formula Va

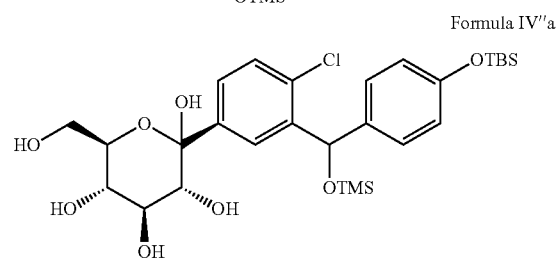

Formula IV''a d) converting compound of Formula IV''a to a compound of Formula IVa.

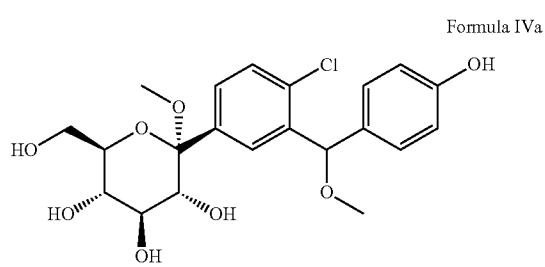

Formula IVa e) reducing the compound of Formula IVa in to a compound of formula IIIa; and

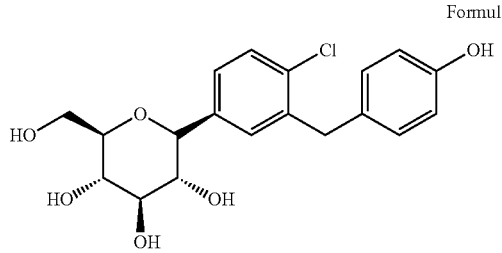

Formula IIIa f) reacting compound of Formula III with compound of Formula II to obtain empagliflozin of Formula I

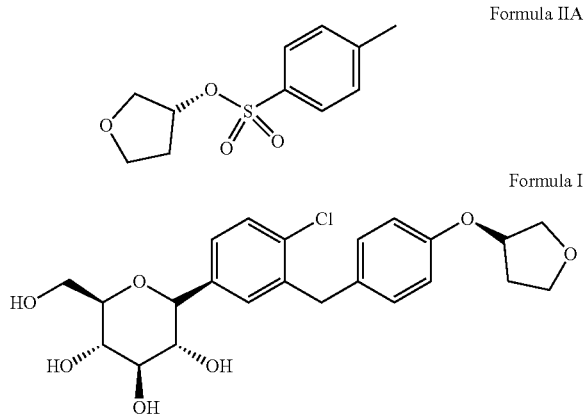

Formula IIA

Formula I

In another aspect, the present invention provides a process for the preparation of empagliflozin of Formula I or its co-crystals, solvates and/or their polymorphs thereof, comprising:
 a) providing a solution of empagliflozin of Formula I in an organic solvent,
 b) adding suitable co-crystal former to the step (a) solution,
 c) isolating empagliflozin co-crystal of Formula Ia,
 d) neutralising empagliflozin co-crystal of Formula Ia using a suitable acid or base; and
 e) converting pure empagliflozin of Formula I to its pharmaceutically acceptable polymorphs thereof;
wherein the suitable co-crystal former is selected from the group comprising DL-pipecolic acid, D-pipecolic acid, L-pipecolic acid, ammonia, nicotinic acid, isonicotinic acid, pyridine, pyrazine-2-carboxylic acid, imidazole, morpholine, proline and the like.

In another aspect, the present invention provides a process for the preparation of crystalline empagliflozin of Formula I or its co-crystals, solvates and/or their polymorphs thereof, comprising:
 a) providing a solution of crude empagliflozin of Formula I obtained from the process described as above, in one or more organic solvents,
 b) cooling the solution to precipitation; and
 c) isolating crystalline empagliflozin of formula I In accordance with another aspect, the present invention provides a pharmaceutical composition comprising empagliflozin of Formula I or its co-crystals, solvates and/or their polymorphs thereof, prepared by the processes of the present invention and at least one pharmaceutically acceptable excipient.

DETAILED DESCRIPTION OF THE INVENTION

Figure 1:
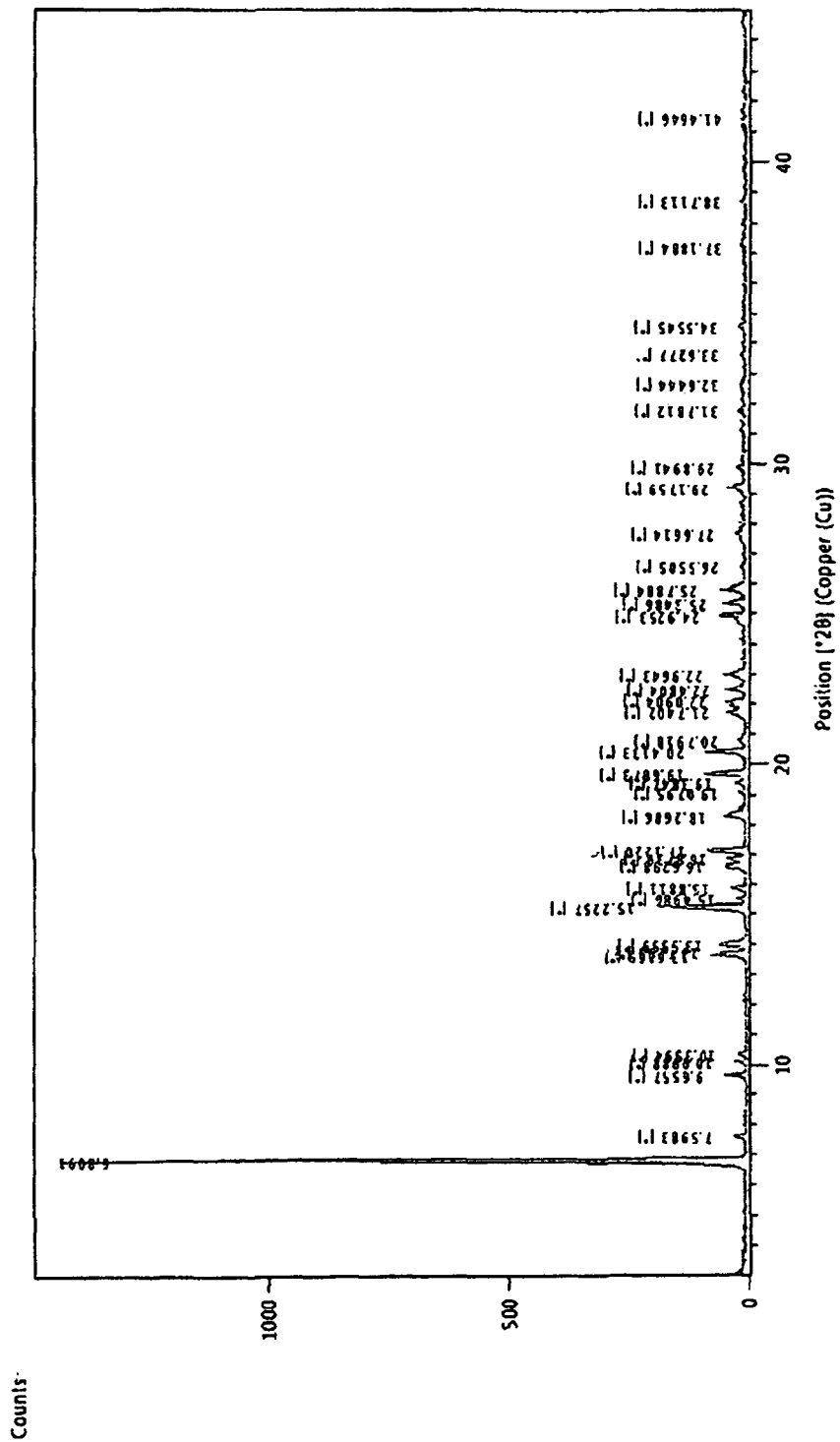
FIG. 01 is the PXRD spectrum of compound of Formula VII

The present invention provides a process for the preparation of empagliflozin of Formula I or its co-crystals, solvates and/or their polymorphs thereof by using novel intermediates.

In an embodiment, the present invention provides a process for the preparation of empagliflozin of Formula I or its co-crystals, solvates and/or their polymorphs thereof;

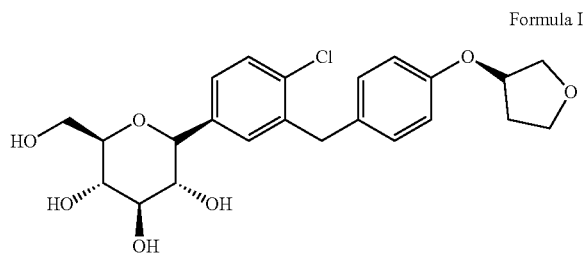

Formula I comprising:
 a) reacting an aldehyde compound of Formula IX with a compound of Formula VIII or reactive derivative thereof, to obtain a compound of formula VII or a reactive derivative thereof;

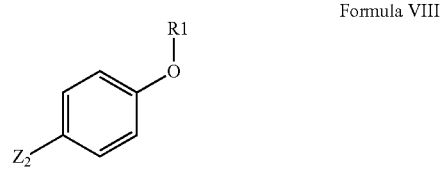

Formula VIII

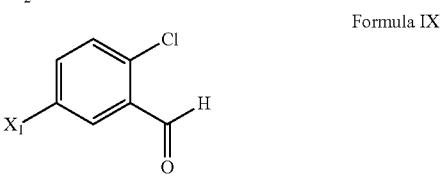

Formula IX

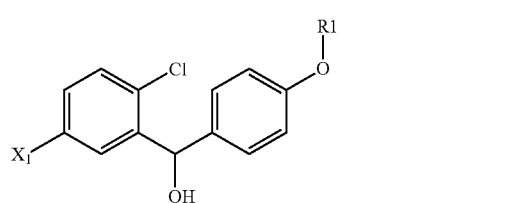

Formula VII wherein "X₁" and "X₂" independently represents a suitable leaving group and R₁ represents hydrogen or a suitable hydroxyl protecting group;

b) optionally protecting the hydroxyl group of compound of Formula VII to obtain a compound of Formula VI; wherein R₁ and R₂ independently represents hydrogen or a suitable hydroxyl protecting group;

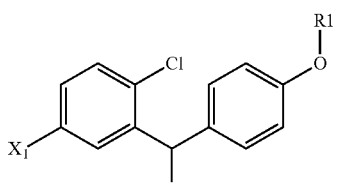

Formula VII

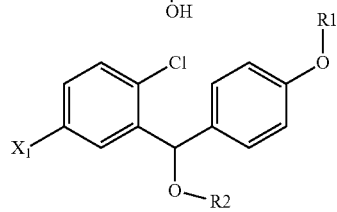

Formula VI c) condensing the compound of Formula VII or its protected derivative of Formula VI with glucono lactone of compound of Formula V to obtain a compound of formula IV'''; wherein R₁, R₂, P₁, P₂, P₃, and P₄ independently represents hydrogen or a suitable hydroxyl protecting group;

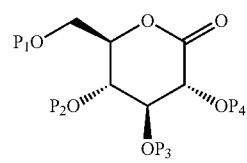

Formula V

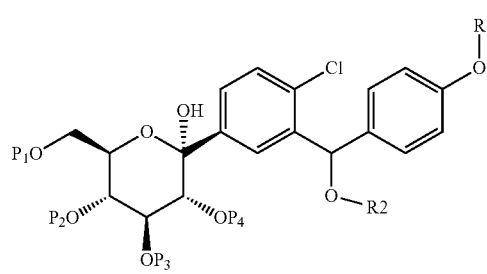

Formula IV''' d) converting the compound of Formula IV''' to a compound of Formula IV; wherein R3 represents an alkyl group;

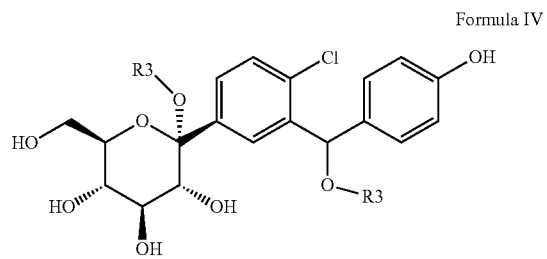

Formula IV e) reducing the compound of Formula IV in to a compound of Formula III; and

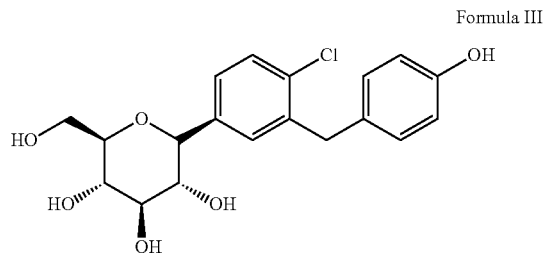

Formula III f) reacting the compound of Formula III with a compound of Formula II to obtain empagliflozin of Formula I;

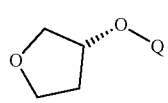

Formula II

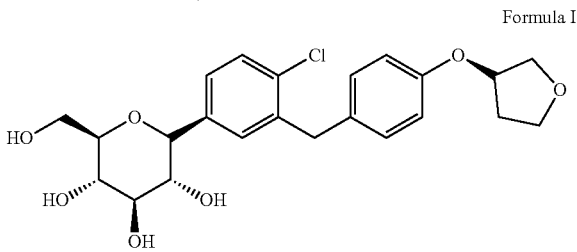

Formula I wherein "Q" represents a suitable leaving group.

Unless otherwise specified the term "alkyl" used herein the specification represents $C_{1-12}$ alkyl and is selected from but not limited to, methyl, ethyl, propyl, isopropyl, iso butyl, isoamyl and the like.

Unless otherwise specified the term "aryl" used herein the specification represents $C_{6-18}$ aryl and is selected from but not limited to phenyl, naphthyl and the like.

Unless otherwise specified the term "X₁" and "X₂" used herein are represents a suitable leaving group and are selected from but not limited to halogen such as chloro, bromo, iodo and the like; methanesulfonyloxy, p-toluenesulfonyloxy or pefluoroalkyl sulfonate and the like.

Unless otherwise specified the substituents R₁ and R₂ independently represents hydrogen or a suitable hydroxyl protecting group which includes but is not limited to alkyl, acetyl, pivaloyl, methoxymethyl, benzyl, benzoyl, tert-butoxycarbonyl, benzyloxycarbonyl, tetrahydropyranyl, trimethylsilyl (TMS), triethylsilyl (TES), t-butyl(dimethyl)silyl (TBS), t-butyl(diphenyl)silyl (TBDPS), tri(isopropyl)silyl (TI PS), 2-(trimethylsilyloxy)ethyl, tert-Butyl 2,2,2-trichloroacetimidate, 4-Methoxybenzyl-2,2,2-trichloroacetimidate, Benzyl 2,2,2-trichloroacetimidate, methyl 2,2,2-trichloroacetimidate and O-allyl 2,2,2-trichloroacetimidate and the like.

Unless otherwise specified the substituents "P₁", "P₂", "P₃" and "P₄" represents hydrogen or a "suitable hydroxyl protecting group". Examples of hydroxyl protecting groups include, but are not limited, to alkyl, allyl, pivaloyl, acetyl (Ac), tosyl (Ts), mesyl (Ms), silyl like trimethylsilyl (TMS) or tertiary butyldimethylsilyl (TBS), benzyl (Bn), paramethoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like. Further, the protecting groups for hydroxyl grouos may form acetal or silyl acetal together with adjacent hydroxyl groups.

Unless otherwise specified the term "co-crystals" used herein the specification refers a to crystalline material comprised of two or more unique solids at room temperature, each containing distinctive physical characteristics, such as structure, melting point and heats of fusion.

The starting materials of compound of Formula IX or compound of Formula VIII are known compound(s), and can be prepared by any of conventional methods reported in the art.

Step (a) of the foregoing process involves reacting a compound of Formula IX with a compound of Formula VIII or a reactive derivative thereof in presence of suitable organolithium compound and an organic solvent to obtain a compound of Formula VII or a reactive derivative thereof;

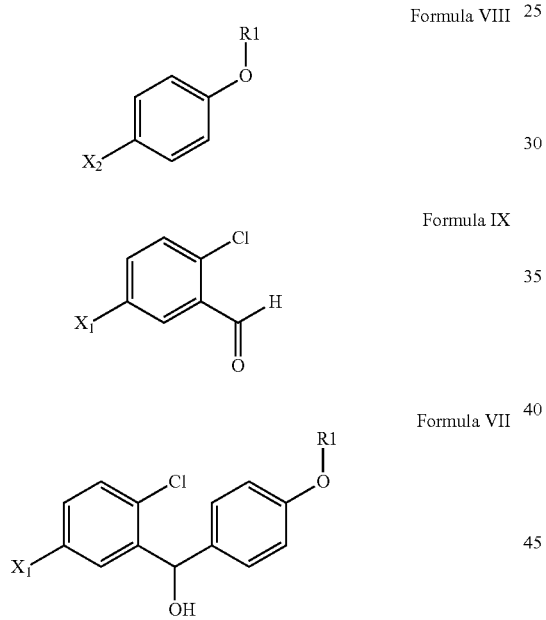

Formula VIII

Formula IX

Formula VII wherein "$X_1$", "$X_2$" and "$R_1$" are as defined above; preferably "$X_1$" and "$X_2$" independently represents bromo and "$R_1$" represents tertiary butyldimethylsilyl (TBS).

Typically the reaction involves, subjecting compound of Formula VIII or reactive derivative thereof in an organic solvent to halogen-metal exchange reaction with suitable organo lithium compound; thereby obtaining the corresponding lithiated aromatic group. Thus resulted metallised aromatic compound may by directly or after further transmetallation, is added to a compound of Formula IX to obtain diphenylmethanol compound of Formula VII.

Advantageously the compound of Formula VIII or reactive derivative thereof first treated with a water immiscible organic solvent and then the solvent may be removed by evaporation to limit the moisture content in the reaction to acceptable limits. The water immiscible organic solvent used herein is selected from the group consisting of toluene, xylene, ethyl acetate, diethyl ether, diisopropyl ether, 2-butanone, pentane, dichloromethane, chloroform, 1,2-dichloroethane, heptane, hexane and the like; preferably toluene.

The resulted compound of Formula VIII or reactive derivative thereof is reacted with a suitable organo lithium compound and further with a compound of Formula IX to obtain diphenylmethanol compound of Formula VII or a reactive derivative thereof in a suitable organic solvent at a temperatures between 0 and −100° C., particularly between −10 and −80° C.

The organic solvent used herein includes but is not limited to ethers, aromatic hydrocarbons, cyclic hydrocarbons, halogenated hydrocarbons and the like and mixtures thereof. Ethers include, but are not limited to tetrahydrofuran, dimethyl ether, diisopropyl ether, methyl tertiary butyl ether, and the like; aromatic hydrocarbons include but are not limited toluene, xylene and the like; cyclic hydrocarbons include, but are not limited n-hexane, n-heptane, cyclohexane and the like; halogenated hydrocarbons include, but are not limited to methylene chloride, ethylene chloride, chloroform and the like; and mixtures thereof. Preferably, the organic solvent is tetrahydrofuran.

The suitable organo lithium compound used herein include but not limited to Ethyl lithium; n-, sec- or tert-butyl lithium; Lithium amide; Lithium bis(trimethylsilyl)amide; Lithium tert-butoxide; Lithium cyclopentadienide; Lithium diisopropylamide; Lithium ethoxide; Lithium methoxide; Lithium isopropoxide or Phenyllithium. Preferably, the organo lithium compound is n-butyl lithium.

In another embodiment, the compound of Formula VII thus formed herein is represented as follows:

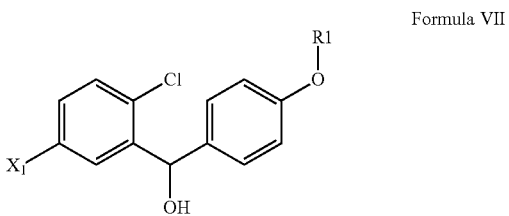

Formula VII wherein "$X_1$" represents a suitable leaving group and $R_1$ represents hydrogen or a suitable hydroxyl protecting group.

In another embodiment, the present invention provides a compound of Formula VII

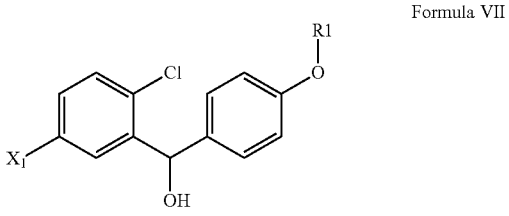

Formula VII wherein "$X_1$" represents a suitable leaving group and $R_1$ represents hydrogen or a suitable hydroxyl protecting group.

In another embodiment, the present invention provides a compound of Formula VII

Formula VII

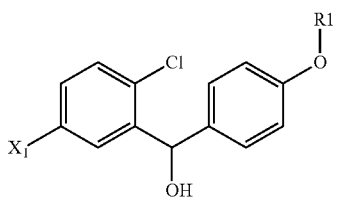

wherein X₁ represents a suitable leaving group, which is selected from the group consisting of chloro, bromo, iodo, methane sulfonyloxy, p-toluenesulphonyloxy or perfluoroalkylsulfonate; and R₁ represents hydrogen or a suitable hydroxyl protecting group which includes but is not limited to alkyl, acetyl, pivaloyl, methoxymethyl, benzyl, benzoyl, tert-butoxycarbonyl, benzyloxycarbonyl, tetrahydropyranyl, trimethylsilyl, triethylsilyl, t-butyl(dimethyl)silyl, t-butyl(diphenyl)silyl, tri(isopropyl)silyl, 2-(trimethylsilyloxy)ethyl, tert-Butyl 2,2,2-trichloroacetimidate, 4-Methoxybenzyl-2,2,2-trichloroacetimidate, Benzyl 2,2,2-trichloroacetimidate, Methyl 2,2,2-trichloroacetimidate and O-Allyl 2,2,2-trichloroacetimidate and the like.

In another embodiment, the present invention provides a compound of Formula VII

Formula VII

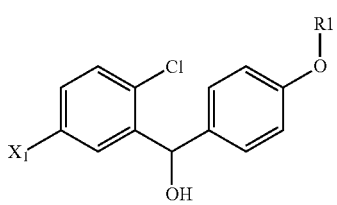

wherein the X₁ is bromo and the R₁ is t-butyl(dimethyl)silyl.

The compound of Formula VII thus obtained by the process of the present invention generally may contain the following compounds as an impurity. These impurities tend to react in the same sequential manner to generate the corresponding impurities in each stage of the synthesis, as a result getting reduced yields and less pure compounds, which require repetitive purifications to separate these impurities from each intermediate stage as well as the final API. These multiple purifications in each stage makes the process lengthy and unviable for commercial operations.

Formula A

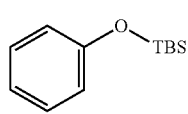

Des bromo Impurity

Formula B

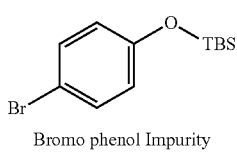

Bromo phenol Impurity

Formula C

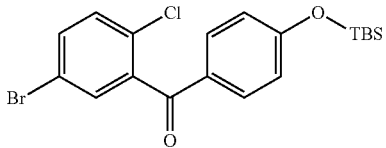

Keto Impurity

Formula D

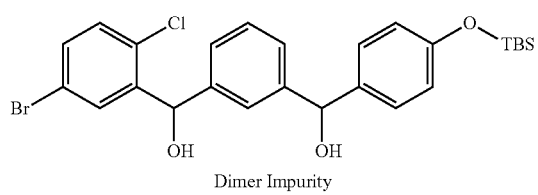

Dimer Impurity

In order to avoid repetitive purifications to separate these impurities from the each intermediate stage as well as the final API, removal of these impurities at the source stage itself is having advantage.

The present inventors have found that purification of compound of Formula VII using a modified isolation involving novel solvent system efficiently removing the above impurities and getting high pure compound of Formula VII thereby getting high pure empagliflozin API using the pure compound of Formula VII.

Thus the present invention involves the purification of compound of Formula VII, in order to avoid repetitive purifications to separate impurities in each stage of the synthesis up to the final API. The isolation step involves, after completion of the reaction, the reaction mass is extracted with a water immiscible organic solvent such as ethyl acetate, dichloromethane, 2-methyl-THF, toluene, and the like; preferably the water immiscible organic solvent is ethyl acetate. Thereafter the product containing water immiscible organic solvent may be evaporated under reduced pressure to obtain a compound of Formula VII as residue. The residue so obtained is isolated and purified by using a novel solvent system to obtain a pure compound of Formula VII.

The Compound of Formula VII thus obtained may be used directly or isolated further, before proceeding to next stage. Preferably the compound of Formula VII is isolated as a solid from the reaction mass. The compound of formula VII or reactive derivative thereof can be isolated by any of methods known in the art, for example by doing solvent crystallization. The solvent used for solvent crystallization includes, but are not limited to cyclic hydrocarbons such as n-hexane, n-heptane, cyclohexane, cycloheptane, methyl cyclohexane and the like; preferably used solvent is n-heptane.

In another embodiment, compound of Formula VII or reactive derivative thereof obtained by the process of the invention is having less than 0.1% of each of des bromo impurity of Formula A, bromo phenol impurity of Formula B, keto impurity of Formula C and/or dimer impurity of Formula D as measured by HPLC; preferably less than 0.05%, as measured by HPLC.

In another embodiment, the compound of Formula VII obtained according to the present invention may be used as an intermediate or as a starting material in the preparation of empagliflozin or its co-crystals, solvates and/or their polymorphs thereof.

In another embodiment, the present invention provides a process for the preparation of empagliflozin of Formula I or its co-crystals, solvates and/or their polymorphs thereof from the compound of Formula VII as an intermediate or as a starting material. The compound of Formula VII obtained from the process described as above is optionally protected the hydroxyl group using a suitable hydroxyl protecting group according to step b) of the foregoing process.

The step (b) of the foregoing process involves, protecting the hydroxyl group of compound of Formula VII or a reactive derivative thereof to obtain a compound of Formula VI or reactive derivative thereof using a suitable hydroxyl protecting group in presence of an organic solvent and a base,

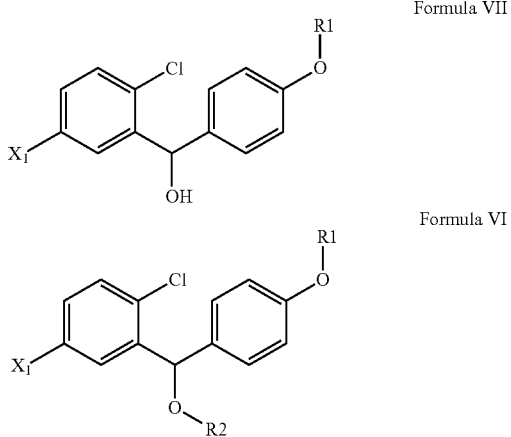

Wherein $X_1$, $R_1$ and $R_2$ are same as defined above; preferably $X_1$ is bromo and $R_1$ is t-butyl(dimethyl)silyl and $R_2$ is trimethylsilyl group (TMS).

Typically the reaction procedure involves, optionally, dissolving compound of Formula VII or reactive derivative thereof in a suitable solvent, followed by treating the resulted solution with a suitable hydroxyl protecting group in presence of base.

The suitable solvent used herein for step b) includes but is not limited to halogenated hydrocarbons, nitriles, ethers, sulfoxides, ketones, amides and mixtures thereof. The halogenated hydrocarbons include, but are not limited to methylene chloride, ethylene chloride, chloroform and the like; nitriles include, but are not limited to acetonitrile, propionitrile and the like; ethers include, but are not limited to tetrahydrofuran, dimethyl ether, diisopropyl ether, methyl tertiary butyl ether, 1,4-dioxane and the like; sulfoxides include, but are not limited to dimethylsulfoxide, diethyl sulfoxide and the like; ketones include, but are not limited to acetone, methyl isobutyl ketone, methyl ethyl ketone and the like; amides include, but are not limited to dimethyl formamide, dimethyl acetamide, N-methyl pyrrolidinone and the like and mixtures thereof. Preferably, the solvent used herein is dichloromethane.

The suitable hydroxyl protecting group is $R_2$—$X_1$, wherein "$R_2$" and "$X_1$" are as defined above. Preferably suitable $R_2$—$X_1$ is trimethyl silyl chloride or tert-butyl dimethyl silyl chloride. The suitable base used herein includes, but is not limited to diethylamine, dimethyl amine, triethylamine, isopropyl ethylamine, diisopropyl amine, diisopropyl ethylamine; N-methyl morpholine, piperidine, pyridine and the like and mixtures thereof. Preferably, suitable base is trimethylamine.

The reactions are carried out between temperature of about 10 and 40° C., preferably between 20° C. and 35° C. And thus resulted compound of Formula VI or reactive derivative thereof may be used directly to the next step, without isolating further.

In another embodiment, the compound of Formula VI thus formed herein is represented as follows:

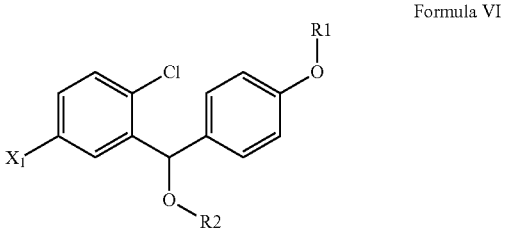

wherein "$X_1$" represents a suitable leaving group and $R_1$ and $R_2$ represents hydrogen or a suitable hydroxyl protecting group.

In another embodiment, the present invention provides a compound of Formula VI

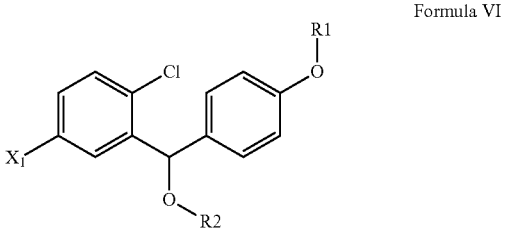

wherein "$X_1$" represents a suitable leaving group and $R_1$ and $R_2$ represents hydrogen or a suitable hydroxyl protecting group.

In another embodiment, the present invention provides a compound of Formula VI

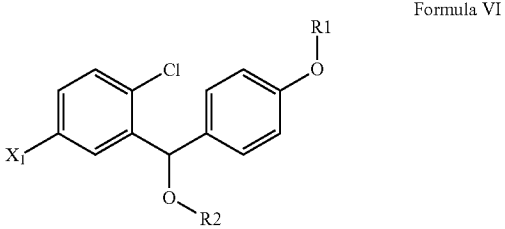

wherein $X_1$ represents a suitable leaving group, which is selected from the group consisting of chloro, bromo, iodo, methane sulfonyloxy, p-toluenesulphonyloxy or perfluoroalkylsulfonate; and $R_1$ and $R_2$ independently represents hydrogen or a suitable hydroxyl protecting group which includes but is not limited to alkyl, acetyl, pivaloyl, methoxymethyl, benzyl, benzoyl, tert-butoxycarbonyl, benzyloxycarbonyl, tetrahydropyranyl, trimethylsilyl, triethylsilyl, t-butyl(dimethyl)silyl, t-butyl(diphenyl)silyl, tri(isopropyl)silyl, 2-(trimethylsilyloxy)ethyl, tert-Butyl 2,2,2-trichloroacetimidate, 4-Methoxybenzyl-2,2,2- trichloroacetimidate, Benzyl 2,2,2-trichloroacetimidate, Methyl 2,2,2-trichloroacetimidate and O-Allyl 2,2,2-trichloroacetimidate and the like.

In another embodiment, the present invention provides a compound of Formula VI

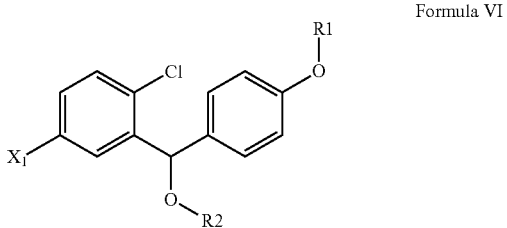

Formula VI wherein the "$X_1$" is bromo and the "$R_1$" is t-butyl(dimethyl)silyl and "$R_2$" is trimethylsilyl.

In another embodiment, the compound of Formula VI obtained according to the present invention may be used as an intermediate or as a starting material in the preparation of empagliflozin or its co-crystals, solvates and/or their polymorphs thereof.

In another embodiment, the present invention provides a process for the preparation of empagliflozin of Formula I or its co-crystals, solvates and/or their polymorphs thereof from the compound of Formula VI as an intermediate or as a starting material.

The compound of Formula VI obtained from the process described as above is converted in to a compound of Formula IV" according to step c) of the foregoing process.

The step (c) of the foregoing process involves condensing compound of Formula VII or its protected derivative of Formula VI with glucono lactone of compound of Formula V in presence of suitable organolithium compound and an organic solvent to obtain compound of Formula IV"; wherein $R_1$, $R_2$, $P_1$, $P_2$, $P_3$, and $P_4$ independently represents hydrogen or a suitable hydroxyl protecting group, which are same as defined above

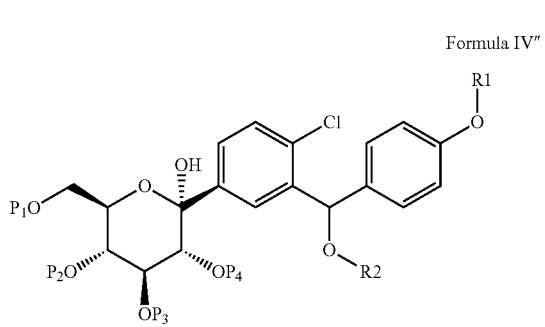

Formula V

Formula IV"

Preferably, wherein the substituents $X_1$ is bromo, $R_1$ is t-butyl(dimethyl)silyl, $R_2$ is trimethylsilyl group and $P_1$, $P_2$, $P_3$, and $P_4$ independently represents trimethylsilyl group.

Typically the condensation reaction involves, subjecting the compound of Formula VII or its protected derivative of Formula VI to halogen-metal exchange reaction with suitable organolithium compound; thereby corresponding lithiated aromatic group is generated, which is thus reacted with glucono lactone compound of Formula V to obtain a compound of Formula IV".

Typically, the condensation reaction may be carried out at temperatures between 0 and −100° C., preferably between −10 and −90° C.

The suitable organo lithium compound used herein for step c) include but is not limited to ethyl lithium; n-, sec- or tert-butyl lithium; Lithium amide; Lithium bis(trimethylsilyl)amide; Lithium tert-butoxide; Lithium cyclopentadienide; Lithium diisopropylamide; Lithium ethoxide; Lithium methoxide; Lithium isopropoxide or Phenyllithium. Preferably, the suitable organo lithium compound is n-butyl lithium.

The organic solvent used herein for step c) includes but is not limited to ethers, aromatic hydrocarbons, cyclic hydrocarbons, halogenated hydrocarbons and the like and mixtures thereof. Ethers include, but are not limited to tetrahydrofuran, dimethyl ether, diisopropyl ether, methyl tertiary butyl ether, and the like; aromatic hydrocarbons include but are not limited toluene, xylene and the like; cyclic hydrocarbons include, but are not limited n-hexane, n-heptane, cyclohexane and the like; halogenated hydrocarbons include, but are not limited to methylene chloride, ethylene chloride, chloroform and the like; and mixtures thereof. Preferably, the organic solvent used herein is toluene, tetrahydrofuran and mixtures thereof.

The resulted compound of Formula IV" thus formed may be isolated as a solid or proceed further without isolating the compound of Formula IV" in to subsequent reactions.

In another embodiment, the compound of Formula IV" thus obtained is used as such for the subsequent reactions without isolating from the reaction mass as solid.

In another embodiment, the compound of Formula IV" thus formed herein is represented as follows:

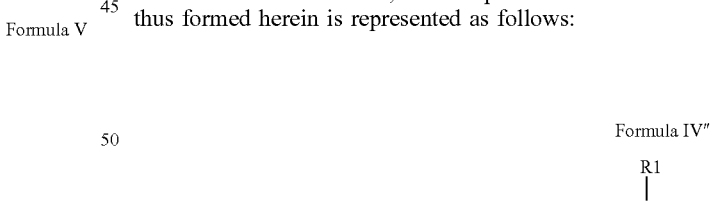

Formula IV"

wherein $R_1$, $R_2$, $P_1$, $P_2$, $P_3$, and $P_4$ independently represents hydrogen or a suitable hydroxyl protecting group, which are same as defined above.

In another embodiment, the present invention provides a compound of Formula IV"

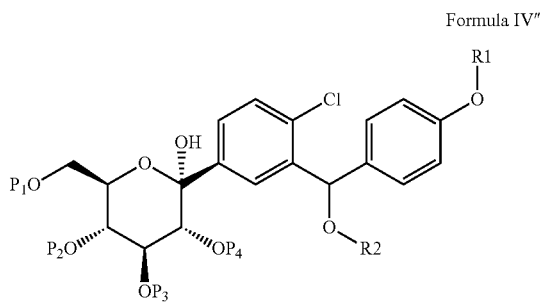

Formula IV″ wherein $R_1$, $R_2$, P, $P_1$, $P_2$, $P_3$ and $P_4$ independently represents hydrogen or a suitable hydroxyl protecting group.

In another embodiment, the present invention provides a compound of Formula IV‴

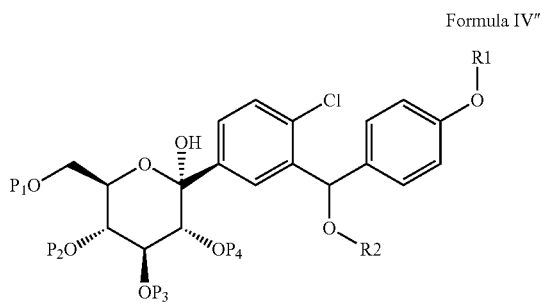

Formula IV‴ wherein $R_1$ and $R_2$ independently represents hydrogen or a suitable hydroxyl protecting group which includes but is not limited to alkyl, acetyl, pivaloyl, methoxymethyl, benzyl, benzoyl, tert-butoxycarbonyl, benzyloxycarbonyl, tetrahydropyranyl, trimethylsilyl, triethylsilyl, t-butyl(dimethyl)silyl, t-butyl(diphenyl)silyl, tri(isopropyl)silyl, 2-(trimethylsilyloxy)ethyl, tert-Butyl 2,2,2-trichloroacetimidate, 4-Methoxybenzyl-2,2,2-trichloroacetimidate, Benzyl 2,2,2-trichloroacetimidate, methyl 2,2,2-trichloroacetimidate and O-allyl 2,2,2-trichloroacetimidate and the like; wherein P, $P_1$, $P_2$, $P_3$ and $P_4$ independently represents hydrogen or a suitable hydroxyl protecting group, wherein the hydroxyl protecting groups are selected from the group consisting of alkyl, allyl, pivaloyl, acetyl (Ac), tosyl, mesyl, silyl like trimethylsilyl (TMS) or tertiary butyldimethylsilyl (TBS), benzyl (Bn), para-methoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM), and the like. Further, the protecting groups for hydroxyl groups may form acetal or silyl acetal together with adjacent hydroxyl groups.

In another embodiment, the present invention provides a compound of Formula IV‴

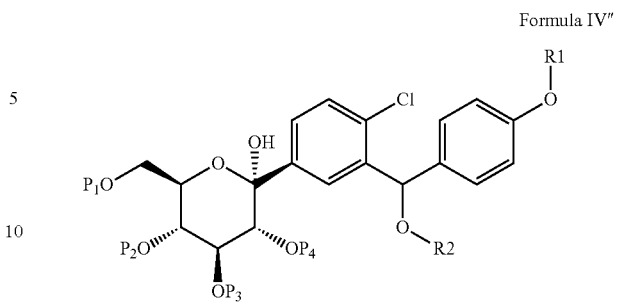

Formula IV″ wherein the $R_1$ is t-butyl(dimethyl)silyl, $R_2$ is trimethylsilyl and each of P, $P_1$, $P_2$, $P_3$ and $P_4$ is trimethylsilyl.

In another embodiment, the compound of Formula IV‴ obtained according to the present invention may be used as an intermediate or as a starting material in the preparation of empagliflozin or its co-crystals, solvates and/or their polymorphs thereof.

In another embodiment, the present invention provides a process for the preparation of empagliflozin of Formula I or its co-crystals, solvates and/or their polymorphs thereof from the compound of Formula IV‴ as an intermediate or as a starting material. The compound of Formula IV‴ obtained from the process described as above is converted in to the compound of Formula IV according to step d) of the foregoing process by glycosidation of compound of formula IV‴ through formation of dihydroxy compound of Formula IV-I as an intermediatery product, wherein the substituents "$R_1$", "$R_2$","$P_1$","$P_2$","$P_3$" and"$P_4$" represents hydrogen or a suitable hydroxyl protecting group.

The step (d) of the foregoing process involves, converting the compound of Formula IV‴ to a compound of Formula IV; wherein $R_3$ represents an alkyl group;

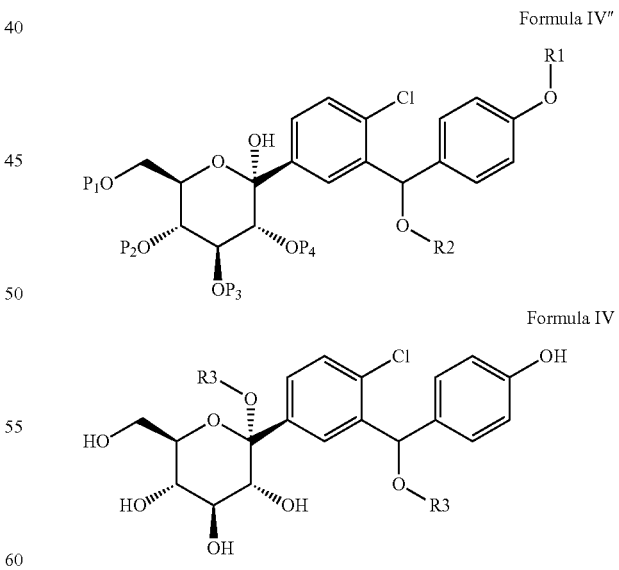

Typically the reaction involves, glycosidation of compound of Formula IV‴ using a suitable acid in presence of a suitable nucleophilic compound such as an alcohol compound.

The suitable acid used in for glycosidation is capable of facilitating deprotection of the hydroxyl groups through removal of the protecting groups "R₁", "R₂", "P₁", "P₂", "P₃" and "P₄", which results dihydroxy compound of Formula IV-I, which is then simultaneously forming corresponding dialkoxy compound of Formula IV using a suitable alcohol group.

The intermediatery dihydroxy compound of Formula IV-I is represented as follows:

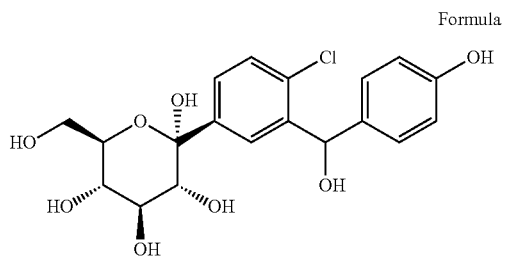

Formula IV-1

The suitable acid used herein for the glycosidation reaction is selected from an organic acid such as formic acid, acetic acid, trifluoroacetic acid, methanesulfonic acid, oxalic acid, p-toluene sulfonic acid and the like; an inorganic acid such as hydrochloric acid, sulfuric acid, nitric acid and the like; and a Lewis acid such as boron trifluoride diethyletherate, scandium (III) trifluoromethanesulfonate, titanium (IV) isopropoxide, tin (IV) chloride, zinc (II) bromide, and zinc (II) chloride; preferably the glycosidation reaction is carried out by using methane sulfonic acid or hydrochloric acid.

Further the alcohol used for the glycosidation reaction is $C_{1-12}$ alcohol, preferably is selected from methanol, ethanol, isopropanol and 2-methoxy ethanol and the like.

The glycosidation reaction is advantageously carried out at a temperature of about 20° C. to about 65° C.; preferably at about 25° C. to about 35° C.

Because of intrinsic fragility of empagliflozin, due to its high chirality, empagliflozin synthetic procedures as described in the art contained relatively large amounts of impurities. For example the process disclosed under the '449 patent results in the formation of 6:1 mixture of β/α anomer during condensation reaction of glucano lactone moiety with biaryl compound, which requires additional step of acylation of hydroxyl groups using acetic anhydride, followed by recrystallization of the product using ethanol, and converting to required pure β-anomer by neutralization of acetyl derivative with a solution of potassium hydroxide in methanol, thus requires multiple steps, multiple solvents for removal of α-anomer, which makes the process not viable for large scale manufacturing.

In order to avoid multiple steps, multiple solvents for removal of α-anomer impurity; after completion of the reaction, the present invention involves extracting the compound of Formula IV or reactive derivative thereof, with an organic solvent such as carbon tetrachloride, chloroform, cyclohexane, 1,2-dichloroethane, dichloromethane, diethyl ether, dimethyl formamide, ethyl acetate, heptane, hexane, methyl-tert-butyl ether, pentane, benzene, toluene, 2,2,4-trimethylpentane, 2-methyl-THF and the like. Preferably 2-Methyl THF or ethyl acetate is used as solvent for extracting the compound of Formula IV or reactive derivative thereof. Thereafter the product containing an organic solvent may be evaporated under vacuum, which may be further purified by using second organic solvent.

In a preferred embodiment, the quality of compound of Formula IV or reactive derivative thereof may be improved by purification using a second organic solvent.

The second organic solvent with which the compound of Formula IV may advantageously treated before proceeding to next stage, which process includes but are not limited to esters such as methyl acetate, ethyl acetate, isopropyl acetate, n-propyl acetate, n-butyl acetate, t-butyl acetate and the like; alcohols such as methanol, ethanol, isopropanol, n-propanol, n-butanol, isobutanol and the like; ethers such as tetrahydrofuran, dimethyl ether, diisopropyl ether, methyl tertiary butyl ether, 1,4-dioxane and the like; and mixtures thereof; cyclic hydrocarbons such as n-heptane, cyclohexane and the like; and mixtures thereof. Preferably the second organic solvent is n-heptane or cyclohexane.

Thus resulted compound of Formula IV may be used directly or isolated further before proceeding to next stage. Preferably, the compound of Formula IV is used directly in to the next stage.

In another embodiment, the compound of Formula IV-I thus formed herein is represented as follows:

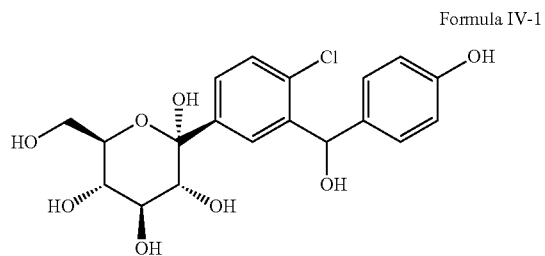

Formula IV-1

In another embodiment, the present invention provides a compound of Formula IV-I

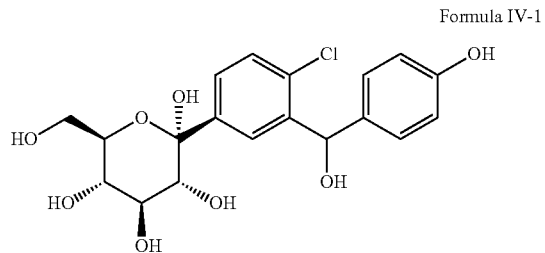

Formula IV-1

In another embodiment, the compound of Formula IV thus formed herein is represented as follows:

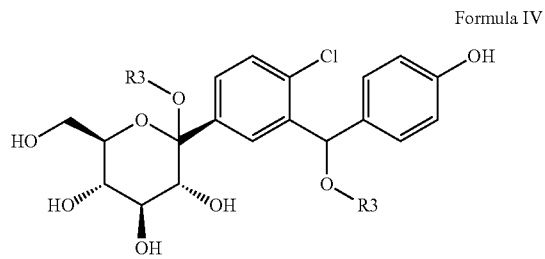

Formula IV wherein R₃ represents an alkyl group.

In another embodiment, the present invention provides a compound of Formula IV

Formula IV

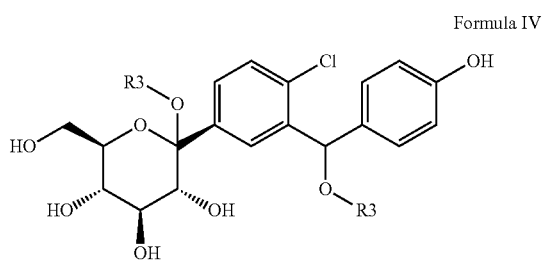

wherein R₃ represents an alkyl group.

In another embodiment, the present invention provides a compound of Formula IV, wherein R$_3$ represents a C$_{1-12}$ alkyl group.

In another embodiment, the present invention provides a compound of Formula IV, wherein R$_3$ represents methyl.

In another embodiment, the compound of Formula IV obtained according to the present invention may be used as an intermediate or as a starting material in the preparation of empagliflozin or its co-crystals, solvates and/or their polymorphs thereof.

In another embodiment, the present invention provides a process for the preparation of empagliflozin of Formula I or its co-crystals, solvates and/or their polymorphs thereof from the compound of Formula IV as an intermediate or as a starting material.

The compound of Formula IV obtained from the process described as above is converted in to the compound of Formula III according to step e) of the foregoing process by reducing the compound of Formula IV using suitable reducing agent.

The step (e) of the forgoing process involves reducing the compound of Formula IV in to a compound of Formula III using a suitable reducing agent in presence of Lewis or Bronsted acid.

Formula III

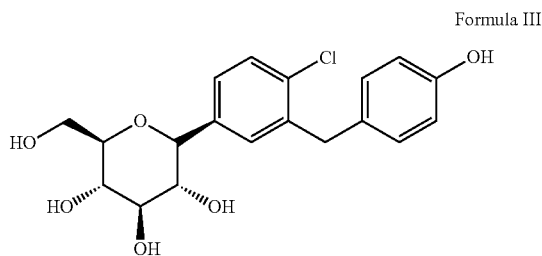

Typically the reduction procedure involves, dissolving compound of Formula IV in a suitable organic solvent, followed by treating the resulted solution with a suitable reducing agent in presence of Lewis or Bronsted acid.

The suitable reducing agents used herein includes, but are not limited to silanes, such as triethyl, tripropyl, triisopropyl or diphenylsilane; sodium borohydride, sodium cyanoborohydride, zinc borohydride, borane reducing agents, lithium aluminium hydride, diisobutylaluminum hydride or samarium iodide. Preferably, the suitable reducing agent is triethylsilane.

The suitable Bronsted acid used herein, includes, but is not limited to hydrochloric acid, toluenesulphonic acid, trifluoroacetic acid, acetic acid and the like. The suitable Lewis acid used herein, includes, but is not limited to boron trifluoride etherate, trimethylsilyltriflate, titanium tetrachloride, tin tetrachloride, scandium triflate, zinc iodide and the like. Preferably, the suitable Bronsted acid is boron trifluoride diethyl etherate.

The organic solvent used for dissolving compound of Formula IV includes but is not limited to halogenated hydrocarbons, nitriles, ethers, sulfoxides, ketones, amides and mixtures thereof. The halogenated hydrocarbons include, but are not limited to methylene chloride, ethylene chloride, chloroform and the like; nitriles include, but are not limited to acetonitrile, propionitrile and the like; ethers include, but are not limited to tetrahydrofuran, dimethyl ether, diisopropyl ether, methyl tertiary butyl ether, 1,4-dioxane and the like; sulfoxides include, but are not limited to dimethylsulfoxide, diethyl sulfoxide and the like; ketones include, but are not limited to acetone, methyl isobutyl ketone, methyl ethyl ketone and the like; amides include, but are not limited to dimethyl formamide, dimethyl acetamide, N-methyl pyrrolidinone and the like and mixtures thereof. Preferably, the organic solvent is acetonitrile, methylene chloride and mixtures thereof.

The reaction is preferably carried out at a temperature of about 60° and −60° C., particularly at about 40 and −40° C.

Preferably, the step (e) reaction can be carried out with a suitable combination of reagents consists, for example, triethylsilane and boron trifluoride etherate in a mixture of acetonitrile, dichloromethane and a mixture thereof.

In another embodiment, after completion of the reaction, extracting the compound of Formula III from the reaction mass with an organic solvent such as, chloroform, cyclohexane, 1,2-dichloroethane, dichloromethane, diethyl ether, dimethyl formamide, ethyl acetate, heptane, hexane, methyl-tert-butyl ether, pentane, benzene, toluene, 2,2,4-trimethylpentane, 2-methyl-THF and the like. Preferably, the suitable organic solvent is ethyl acetate or 2-methyl-THF. Thereafter the product containing organic layer may be evaporated under vacuum, which may be further optionally purified by using a second organic solvent.

In a preferred embodiment, the quality of compound of Formula III or reactive derivative thereof may be improved by purification using a second organic solvent.

In another embodiment, the second organic solvent with which the compound of Formula III may advantageously be purified before proceeding to next stage. The second organic solvent includes but is not limited to esters such as methyl acetate, ethyl acetate, isopropyl acetate, n-propyl acetate, n-butyl acetate, t-butyl acetate and the like; alcohols such as methanol, ethanol, isopropanol, n-propanol, n-butanol, isobutanol and the like; ethers such as tetrahydrofuran, dimethyl ether, diisopropyl ether, methyl tertiary butyl ether, 2-methyl THF, 1,4-dioxane and the like and mixtures thereof; cyclic hydrocarbons such as n-heptane. Preferably, the organic solvent is n-heptane.

Thus the resulted compound of Formula III may be used directly or isolated further before proceeding to next stage.

In another embodiment, the compound of Formula III obtained according to the present invention may be used as an intermediate or as a starting material in the preparation of empagliflozin or its co-crystals, solvates and/or their polymorphs thereof.

In another embodiment, the present invention provides a process for the preparation of empagliflozin of Formula I or its co-crystals, solvates and/or their polymorphs thereof from the compound of Formula III as an intermediate or as a starting material.

The compound of Formula III obtained from the process described as above is converted to empagliflozin according to step f) of the foregoing process by reacting the compound of Formula III with a compound of Formula II.

The step (f) of the foregoing process involves reacting compound of Formula III with compound of Formula II in presence of base and an organic solvent to obtain empagliflozin of formula I;

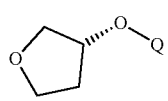
Formula II wherein Q represents a suitable leaving group.

Preferably the suitable leaving group includes, but is not limited to halogen such as chloro, bromo, iodo and the like; methanesulfonyloxy, p-toluenesulfonyloxy or peflouroalkyl sulfonate and the like; more preferably p-toluenesulfonyloxy group.

The suitable base used herein for converting compound of Formula III to compound of Formula I includes but is not limited to sodium carbonate, potassium carbonate, caesium carbonate, sodium bicarbonate, potassium bicarbonate, sodium hydride, potassium ter-butoxide, ammonia, ammonium hydroxide, triethylamine, isopropyl ethylamine, diisopropyl amine, diisopropyl ethylamine, N-methyl morpholine, piperidine and the like and mixtures thereof.

The organic solvent used herein for step f) includes but is not limited to halogenated hydrocarbons, nitriles, ethers, sulfoxides, ketones, amides and mixtures thereof. The halogenated hydrocarbons include, but are not limited to methylene chloride, ethylene chloride, chloroform and the like; nitriles include, but are not limited to acetonitrile, propionitrile and the like; ethers include, but are not limited to tetrahydrofuran, dimethyl ether, diisopropyl ether, methyl tertiary butyl ether, 1,4-dioxane and the like; sulfoxides include, but are not limited to dimethylsulfoxide, diethyl sulfoxide and the like; ketones include, but are not limited to acetone, methyl isobutyl ketone, methyl ethyl ketone and the like; amides include, but are not limited to dimethyl formamide, dimethyl acetamide, N-methyl pyrrolidinone and the like and mixtures thereof. Preferably, the organic solvent is dimethyl formamide or dimethylsulfoxide. The reaction is preferably carried out at a temperature of about 10° and about 80° C., particularly preferably between 20 and 60° C.

After completion of the reaction, the reaction mass may be extracted with a suitable water immiscible organic solvent by adding a mixture of water and water immiscible organic solvent to the reaction mass to separating the empagliflozin from the reaction mass. The water immiscible organic solvent includes, but is not limited to chloroform, dichloromethane, diethyl ether, 2-methyl tetrahydrofuran, ethyl acetate, cyclohexane, heptane, hexane, methyl-tert-butyl ether, toluene, and the like. Preferably, the water immiscible organic solvent is 2-methyl tetrahydrofuran. Thereafter the product containing organic layer may be evaporated under vacuum, and optionally proceed further to the next stage directly as such or upon isolating.

In a preferred embodiment empagliflozin may be used as such to the next stage to obtain empagliflozin of Formula I or its co-crystals, solvates and/or their polymorphs thereof.

In another embodiment, the present invention provides a process for the preparation of crystalline empagliflozin of Formula I or its co-crystals, solvates and/or their polymorphs thereof, comprising:

a) providing a solution of empagliflozin of Formula I obtained in step (f), in one or more organic solvent
b) cooling the solution to precipitation; and
c) isolating crystalline empagliflozin.

The organic solvents used herein under step (a) for dissolving empagliflozin include but is not limited to methanol, ethanol, n-butanol, acetonitrile, dichloromethane or mixture of these solvents with water; preferably n-butanol. The solution may be formed by heating the mixture at a temperature of about 30° C. to about reflux temperature, preferably about 45° C. to about 95° C. The crystalline empagliflozin can be isolated by any known techniques such as cooling the solution to precipitation, crystallization and the like. Preferably the crystalline empagliflozin is isolated by cooling the solution to precipitation followed by filtration.

In another embodiment, the present invention provides a process for preparation of empagliflozin of Formula I or its co-crystals, solvates and/or their polymorphs thereof, comprising purifying the empagliflozin obtained by the process described just as above, by forming a suitable co-crystal of empagliflozin and followed by neutralization of the resulted empagliflozin co-crystal.

In another embodiment, the compound of Formula II or reactive derivatives thereof is purified, prior to subjecting to reaction it with a compound of Formula III, in order to enhance the optical purity of final API.

In another embodiment, the present invention further provides pure compound of Formula II, comprising:

Formula II a) providing a solution comprising compound of Formula II in an organic solvent,
b) cooling the solution to precipitation, and
c) isolating the pure compound of Formula II The step a) of providing a solution of compound of Formula II in organic solvent includes heating to dissolve the compound of Formula II in an organic solvent such as ethyl acetate, dichloromethane, diethyl ether and the like, at a temperature of about 25° C. to 60° C. preferably at about 35° C. to 50° C.; followed by cooling the resultant reaction solution to precipitation at a temperature of less than about 20° C. The precipitated compound of Formula II can be recovered by any conventional techniques known in the art, for example filtration.

In another embodiment, pure compound of Formula II, having optical purity of 99.0% ee or more obtained according to the present invention can be used as an intermediate or as a starting material in the preparation of empagliflozin of Formula I or its co-crystals, solvates and/or their polymorphs thereof.

In another embodiment, the compound of Formula VII, obtained by the aforementioned process, have a chemical purity of at least about 95%, as measured by HPLC, preferably at least about 98%, as measured by HPLC and more preferably at least about 98.5%, as measured by HPLC; and contains less than 0.5% of total impurities, which include Impurity A, Impurity B and Impurity C as measured by HPLC; preferably less than 0.3%, as measured by HPLC; and contains less than 1.5% of dimer impurity of Formula D as measured by HPLC.

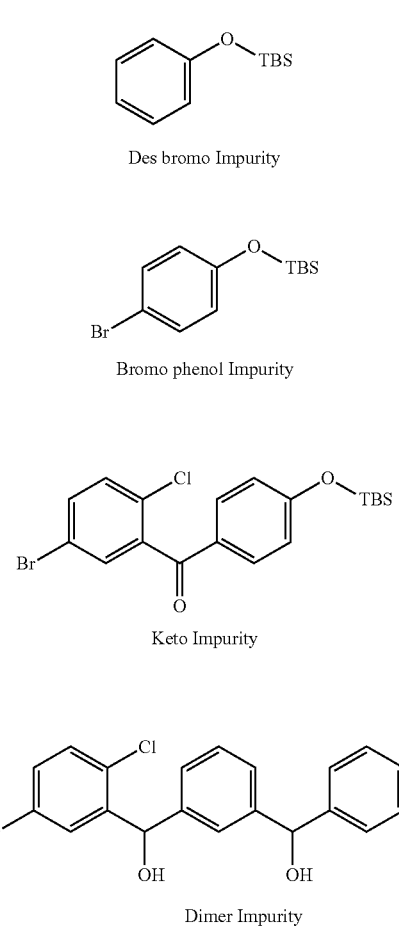

Des bromo Impurity — Formula A

Bromo phenol Impurity — Formula B

Keto Impurity — Formula C

Dimer Impurity — Formula D

In another embodiment, the compound of Formula VII is having less than 0.1% of each of impurity of Impurity A, Impurity B and Impurity C as measured by HPLC; preferably less than 0.05%, as measured by HPLC.

In another embodiment, the compound of Formula VII is having less than 2% of dimer impurity of impurity D, as measured by HPLC; preferably less than 1.5%, as measured by HPLC.

In another embodiment, the present invention provides a compound of Formula VII characterized by PXRD spectrum substantially in accordance with FIG. 01.

Figure 2:
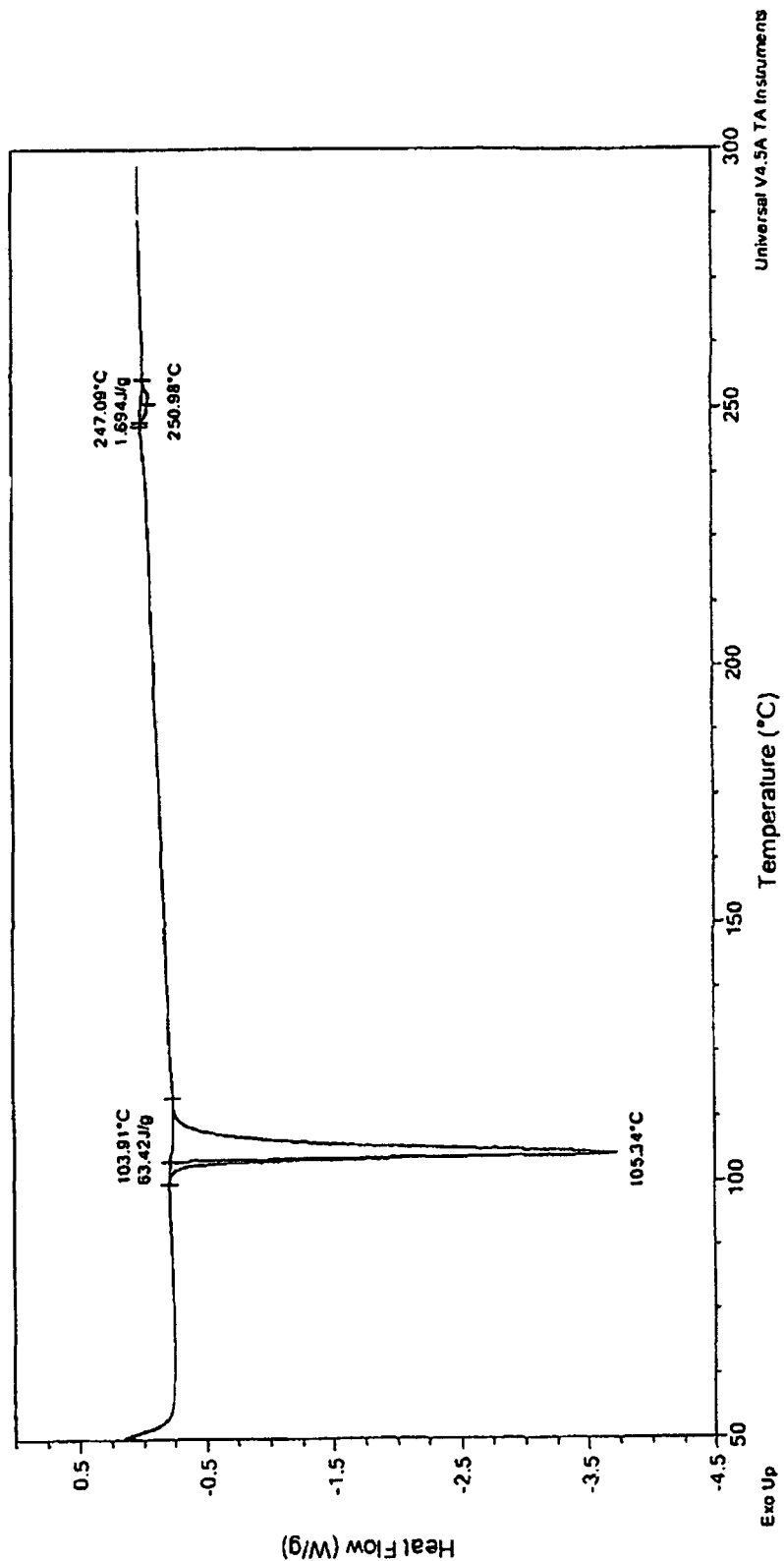
FIG. 02 is the DSC compound of Formula VII

In another embodiment, the present invention provides a compound of Formula VII characterized by a DSC thermogram substantially in accordance with FIG. 02.

Figure 3:
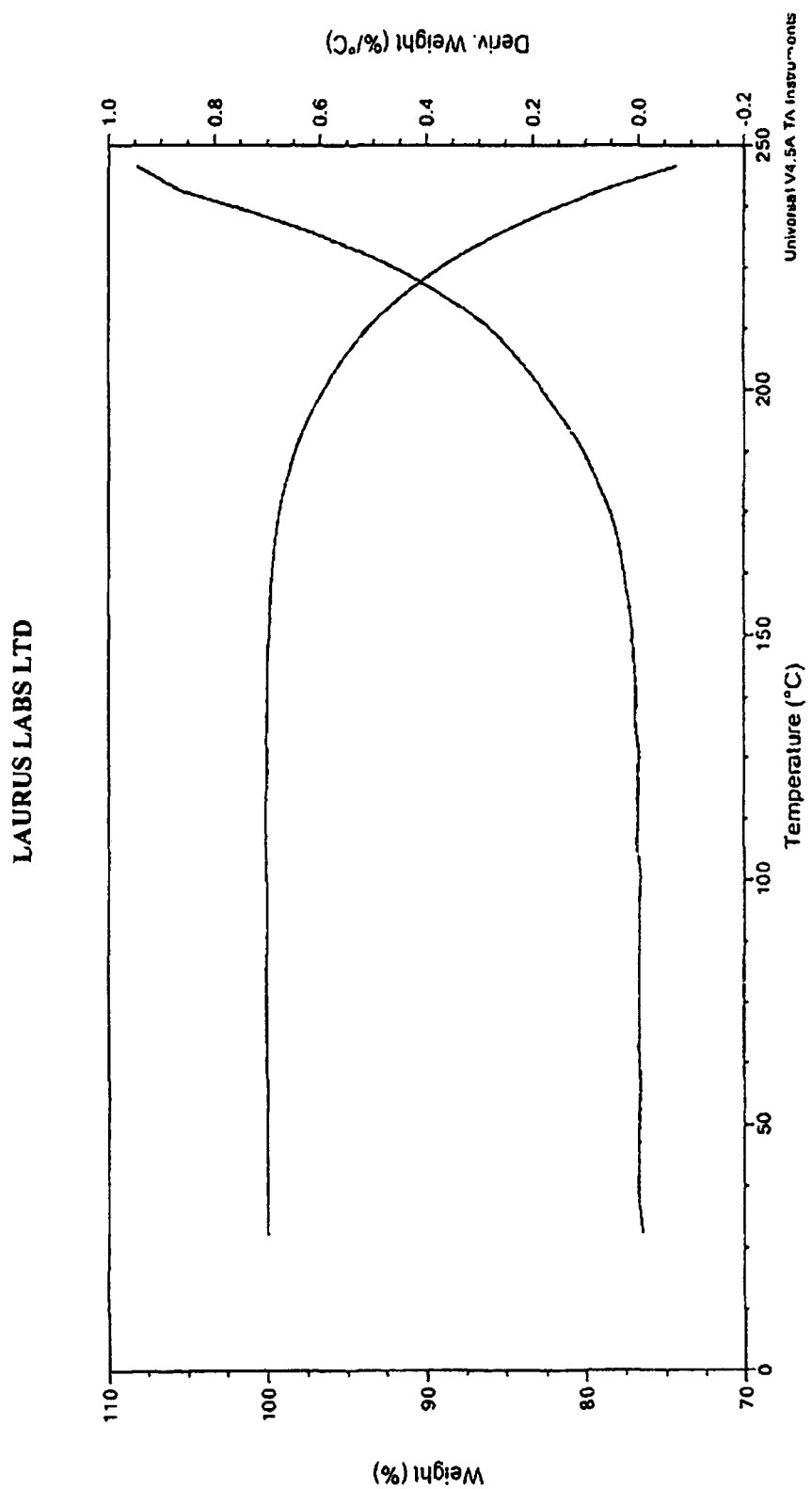
FIG. 03 is the TGA of compound of Formula VII

In another embodiment, the present invention provides a compound of Formula VII characterized by a TGA substantially in accordance with FIG. 03.

In accordance with another embodiment, the present invention provides a process for the preparation of empagliflozin using one or more of the novel intermediates of Formula VII, Formula VI, Formula IV, Formula IV" or Formula IV-1.

In another embodiment, the present invention provides a process for the preparation of empagliflozin of Formula I or its co-crystals, solvates and/or their polymorphs thereof;

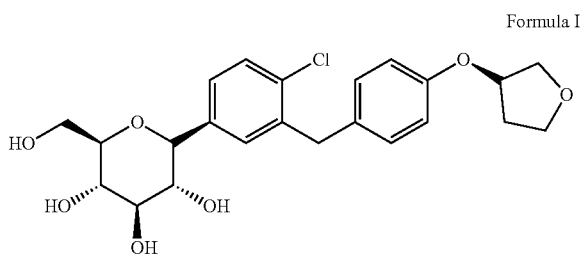

Formula I comprising:

a) reacting a compound of Formula IXa with a compound of Formula VIIIa to obtain a compound of Formula VIIa;

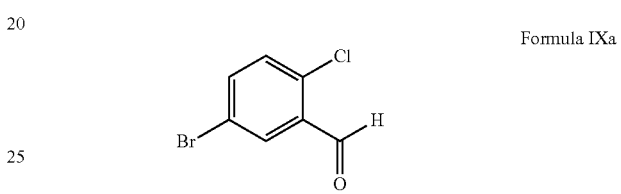

Formula IXa

Formula VIIIa

Formula VIIa b) converting the compound of Formula VIIa to compound of Formula VIa

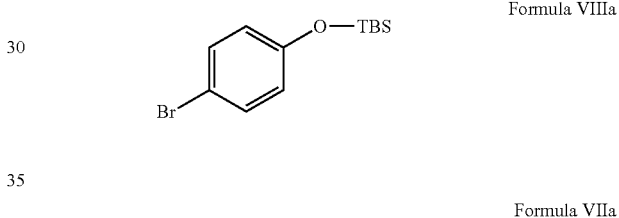

Formula VIIa

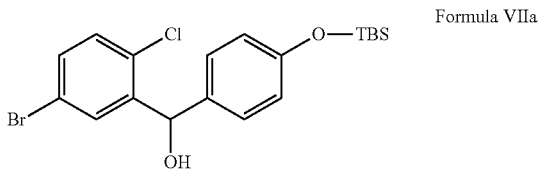

Formula VIa c) condensing the compound of Formula VIa with glucono lactone of compound of Formula Va to obtain compound of formula IV"a

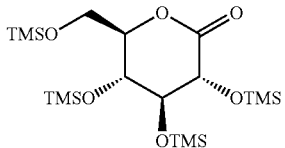
Formula Va

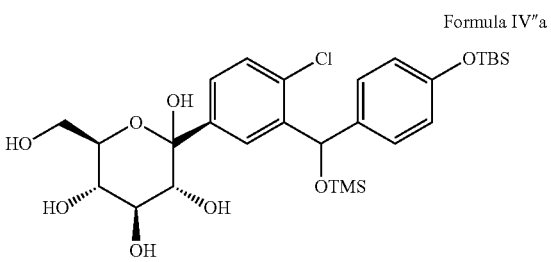
Formula IV"a d) converting compound of Formula IV"a to a compound of Formula IVa.

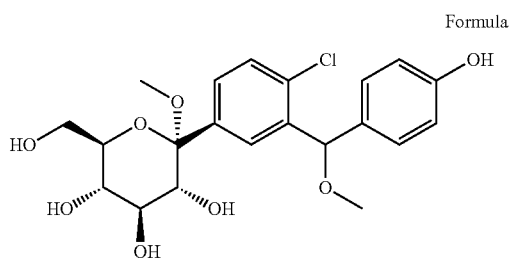
Formula IVa e) reducing the compound of Formula IVa in to a compound of formula IIIa; and

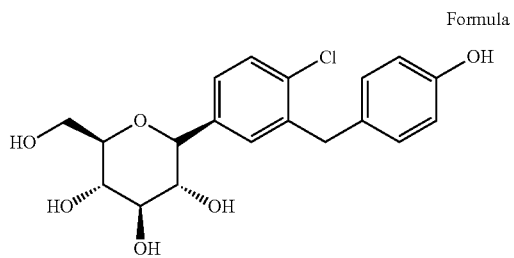
Formula IIIa f) reacting compound of Formula III with compound of formula II to obtain empagliflozin of Formula I

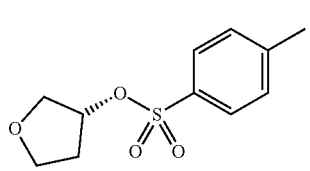
Formula IIA

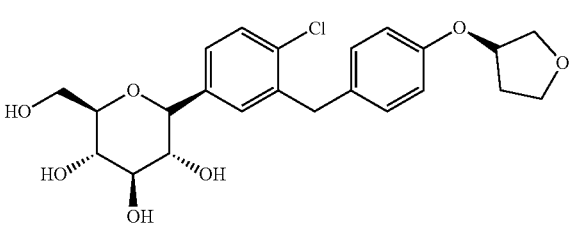
Formula I

In another embodiment, the present invention provides a process for the preparation of empagliflozin of Formula I or its co-crystals, solvates and/or their polymorphs thereof, comprising:
a) providing a solution of empagliflozin of Formula I in an organic solvent,
b) adding suitable co-crystal former to the step (a) solution,
c) isolating empagliflozin co-crystal of Formula Ia,
d) neutralising empagliflozin co-crystal of Formula Ia using a suitable acid or a base; and
e) converting pure empagliflozin of Formula I to its pharmaceutically acceptable polymorphs thereof;
wherein the suitable co-crystal former is selected from the group comprising DL-pipecolic acid, D-pipecolic acid, L-pipecolic acid, ammonia, nicotinic acid, isonicotinic acid, pyridine, pyrazine-2-carboxylic acid, imidazole, morpholine, proline and the like.

The organic solvent used herein under step (a) for dissolving empagliflozin of Formula I obtained according process of the present invention, includes but is not limited to methanol, ethanol, n-butanol, acetonitrile, dichloromethane or mixtures thereof.

The step (a) reaction of providing a solution of empagliflozin in an organic solution, includes heating to dissolve the empagliflozin in an organic solvent at a temperature of about 45° C. to 100° C.; preferably at about 75° C. to about 90° C.; followed by adding co-crystal former to the resultant step (a) solution.

Thus resulted empagliflozin co-crystal can be isolated by precipitating empagliflozin co-crystal solution through cooling to a temperature of less than 40° C. The precipitated empagliflozin co-crystal can be recovered by any conventional techniques known in the art, for example filtration. Typically, if stirring is involved, the temperature during stirring can range from about 25° C. to about 40° C. The resultant product may optionally be further dried at suitable temperatures i.e. about 30° C. to about 80° C.

Step (d) of neutralization of empagliflozin co-crystal of Formula Ia involves dissolving empagliflozin co-crystal of Formula Ia in a suitable solvent followed by neutralization of the resulted solution with a suitable base such as sodium carbonate, potassium carbonate, sodium bicarbonate, potassium bicarbonate, ammonia, ammonium hydroxide, triethylamine, isopropyl ethylamine, diisopropyl amine, diisopropyl ethylamine, N-methyl morpholine, piperidine and the like and mixtures thereof; or a suitable acid such as hydrocholic acid, hydrobromic acid, sulphuric acid and the like.

The solvent used for dissolving empagliflozin co-crystal of Formula Ia is selected from methanol, ethanol, n-butanol, dichloromethane, acetonitrile or water or mixtures thereof.

Pure empagliflozin may be isolated from the reaction mass by methods known in the art, for example, the product containing organic layer may be separated followed by distillation of solvent completely under reduce pressure to obtain empagliflozin.

In another embodiment, pure empagliflozin of Formula I obtained by the process of the invention is having chemical purity of at least about 95%, as measured by HPLC, preferably at least about 98%, as measured by HPLC and more preferably at least about 99.5%, as measured by HPLC; and contains less than 0.5% of total impurities, which include Impurity 5, Impurity 6 and other non-polar impurities as measured by HPLC.

Impurity 5 and Impurity 6 are represented as follows:

Desmethoxy Impurity 5

(R)-3-tosyl tetrahydrofuran of Formula IIA
Impurity 6

In an embodiment, empagliflozin of Formula I contains less than 0.5% of total impurities, which include Impurity 5, Impurity 6 and other non-polar impurities as measured by HPLC; preferably less than 0.3% as measured by HPLC, more preferably less than 0.1% as measured by HPLC.

Figure 4:
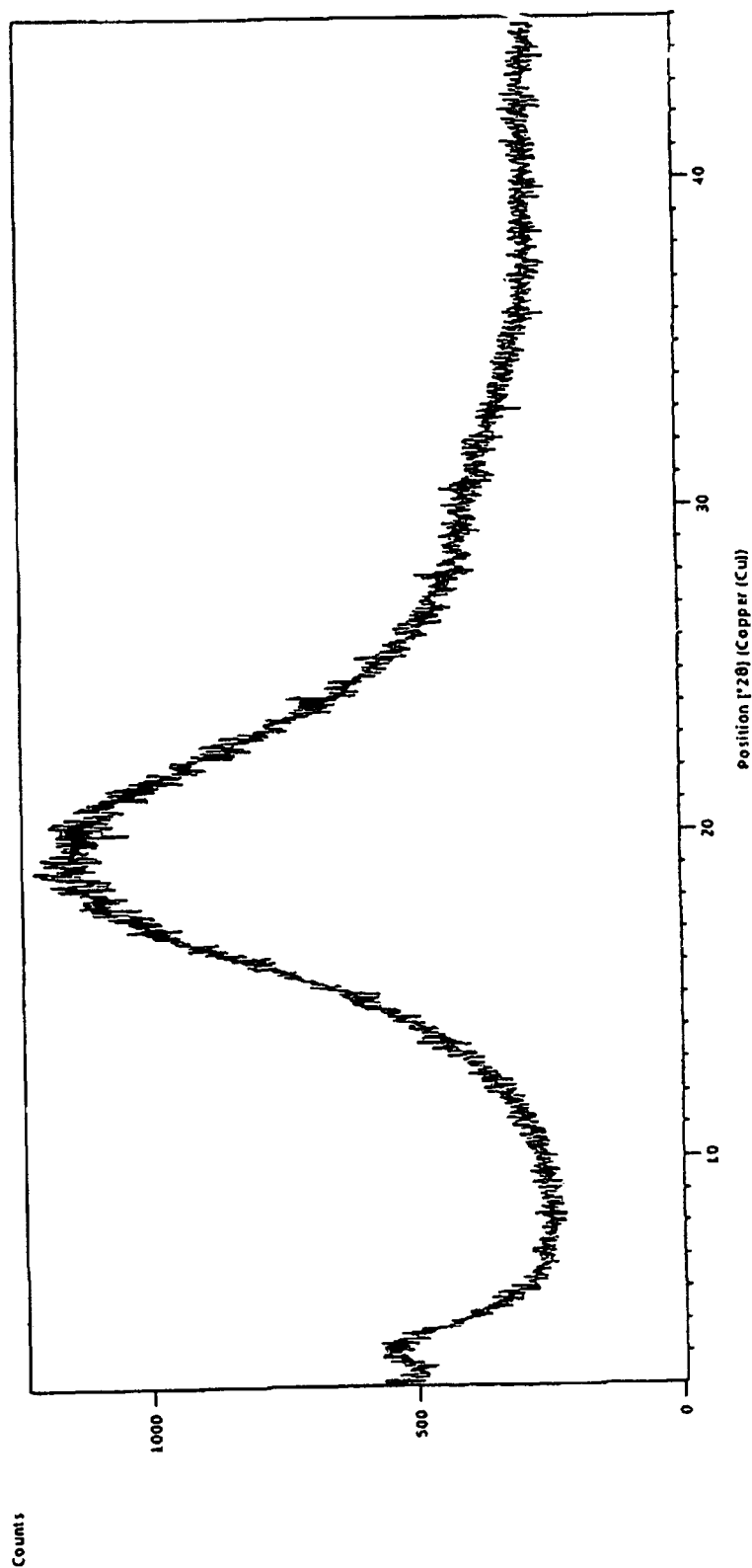
FIG. 04 is the PXRD spectrum of amorphous Empagliflozin

In another embodiment, the present invention provides amorphous empagliflozin characterized by X-Ray powder diffraction (XRD) pattern substantially in accordance with FIG. 04.

In another embodiment, the present invention provides a process for preparation of amorphous empagliflozin comprising:
(a) providing a solution of empagliflozin in one or more organic solvent(s), and
(b) isolating amorphous empagliflozin of Formula I.

The organic solvent used herein for providing a solution of empagliflozin under step (a) includes but is not limited to methanol, ethanol, n-butanol, acetonitrile, dichloromethane; or a mixture of these organic solvents with water.

The solution may be formed by heating the mixture at a temperature of about 30° C. to about reflux temperature, preferably about 45° C. to about 75° C.

The empagliflozin amorphous form can be isolated by any known techniques such as cooling the solution to precipitation, crystallization, solvent precipitation, spray drying, freeze drying, agitated thin film evaporator (ATFE) and the like.

In another embodiment, the present invention provides crystalline Empagliflozin characterized by X-Ray powder diffraction (XRD) pattern.

The X-Ray powder diffraction can be measured using PANalytical X' per³pro X-ray powder Diffractometer equipped with a Cu-anode ([λ]=1.54 Angstrom), X-ray source operated at 45 kV, 40 mA. Two-theta calibration is performed using an NIST SRM 640c Si standard. The sample was analyzed using the following instrument parameters: measuring range=3-45°2θ; step size=0.01°; and Time per step=43 sec.

In another embodiment, the present invention provides empagliflozin obtained by the above process, as analyzed using high performance liquid chromatography ("HPLC") with the conditions are tabulated below:
Column: Sunfire-C18, (150×5) mm, 3.5 µm
Flow rate: 0.7 mL/min
Detection: 225 nm
Injection volume: 10 µL
Run time: 80 min
Elution mode: gradient
Sample solution: 0.3 mg/mL of sample in diluent
Mobile phase: acetonitrile and water
Diluent: acetonitrile
Gradient program

| Time in min | Mobile phase-A (% v/v) | Mobile phase-B (% v/v) |
|---|---|---|
| 0 | 80 | 20 |
| 30 | 65 | 35 |
| 60 | 40 | 60 |
| 70 | 40 | 60 |
| 80 | 80 | 20 |

In accordance with another aspect, the present invention provides a pharmaceutical composition comprising empagliflozin of Formula I or its co-crystals, solvates and/or their polymorphs thereof, prepared by the processes of the present invention and at least one pharmaceutically acceptable excipient.

EXAMPLES

The following non-limiting examples illustrate specific embodiments of the present invention. They are not intended to be limiting the scope of the present invention in any way.

Example 1: Preparation of Compound of Formula VIII (Wherein X2=Bromo; R₁=TBS)

4-bromo phenol (100 gms) and dichloromethane (1000 ml) were added in a round bottom flask at 25-35°. Tertiary butyl dimethysilyl chloride (130.7 grs) and triethyl amine (175.5 gr) were added and maintained with stirring for 10-12 hrs at 25-35° C. Dichloromethane (500 ml) was added to the resulting solution, and the layers were separated. The organic layers were combined, washed with water, 10% brine solution and dried over sodium sulphate. Filtered the compound and further washed with dichloromethane followed by distilled off the solvent under vacuum at below 40° C. to obtain the title compound as a residue.
Yield: 160 gms Example 2: Preparation of Compound of Formula VII (Wherein X1=Bromo; R₁=TBS)

The residue of compound of Formula VIII (~160 gr) was dissolved in toluene (500 ml) at 25 to 35° C. Raised the temperature of the reaction mass to 70-75° C. and distilled of the solvent completely under vacuum at below 75° C. Tetrahydrofuran (500 ml) was added and the reaction mass was allowed to cool to −68 to −85° C., n-butyl lithium (33.2 gms) was added at −68 to −85° C. and stirred for 2-3 hrs at −68 to −85° C. 5-bromo 2-chloro benzaldehyde solution (88.8 gr in tetrahydrofuran 300 ml) was added at −68 to −85° C. and stirred for 2-3 hrs at −68 to −85° C. 10% Ammonium chloride solution (1000 ml) was added to the reaction mass at −20 to 10° C. in 30 min. The temperature of the reaction mass was raised to 25-35° C., settled and the layers were separated. The aqueous layer was extracted with ethyl acetate, combined the organic layers and washed with water, 10% sodium chloride solution and dried over sodium sulphate. The organic layer was distilled completely under vacuum at below 60° C. to obtain a residue, which was purified by n-heptane to obtain the title compound.
Dry wt.: 100 gr;
PXRD, DSC and TGA of title compound is shown in the FIG. 01, FIG. 02 and FIG. 03.
Purity by HPLC: 99.9%; Desbromo silylated phenol impurity 1:0.05%, silylated bromo phenol impurity 2: Not detected; keto compound of impurity 3:0.04%; dimer impurity of impurity 4:0.1%;

Example 3: Preparation of Compound of Formula VI (Wherein X=Bromo; $R_1$=TBS; $R_2$=TMS)

Compound of Formula VII (100 gms) and dichloromethane (1000 ml) were added in a round bottom flask at 25-35° C. Trimethyl silyl chloride (63.5 gr) and triethylamine (70.9 gr) were added and maintained with stirring for 2-3 hrs at 25-35° C. Water was added and the layers were separated. The aqueous layer was extracted with dichloromethane, combined the organic layers and washed with 10% sodium dihydrogen phosphate, followed by 10% brine and dried over sodium sulphate. Filtered the compound and further washed with dichloromethane and distilled off the solvent completely under vacuum at below 45° C., to obtain the title compound as a residue.
Yield: 100 gms Example 4: Preparation of Compound of Formula IV (Wherein $R_1$=Methyl; and $R_2$=Methyl)

The residue of compound of Formula VI was dissolved in toluene (500 ml) at 25-35° C. Raised the temperature of the reaction mass to 70-75° C. and distilled off the solvent completely under vacuum at below 75° C. Tetrahydrofuran (500 ml) was added and the reaction mass was cooled to −68 to −85° C., n-butyl lithium (33.2 gms) was added at −68 to −85° C. and stirred for 2-3 hrs at −68 to −85° C. Silylated sugar solution (93.3 gms in 500 ml toluene) was added at −68 to −85° C. and stirred for 1-2 hrs at −68 to −85° C. After completion of the reaction, a solution of methanesulphonic acid in methanol (68 gms in 300 ml of methanol, which was pre-cooled to −30 to −40° C.) was added to the reaction mass at a temperature of −68 to −85° C. The temperature of the reaction mass was raised to 25-35° C., and water was added, and the layers were separated. The aqueous layer was extracted with methyltetrahydrofuran or ethyl acetate, combined the organic layers and washed with water, 10% sodium chloride solution and dried over sodium sulphate. The organic layer was distilled completely under vacuum at below 60° C. and distilled cyclohexane or n-heptane to obtain the title compound.
Yield: 75 gms Example 5: Preparation of Compound of Formula III The residue of compound of Formula IV was dissolved in a mixture of acetonitrile (300 ml) and dichloromethane (300 ml) at 25-35° C. Triethylsilane (129.2 gr) was added at 25-35° C. and the temperature of the reaction mass was cooled to −25 to −35° C. Borontrifluoride-diethyletherate (158.1 gr) was added to the reaction mass at −40 to −30° C. and stirred for 15 to 20 min. Temperature of the reaction mass was raised to 0° C. and further maintained with stirring for 3 to 4 hrs. Water was added, and the layers were separated and the aqueous layer was extracted with 2-methyltetrahydrofuran or ethyl acetate, combined the organic layers and washed with water, 8% sodium bicarbonate solution and further with 10% brine solution and dried over sodium sulphate. The organic layer was distilled completely under vacuum at below 45° C. and co-distilled with n-heptane and purified by ethyl acetate to obtain the title compound as a solid.
Yield: 40 gms Example 6: Preparation of Empagliflozin of Formula I The residue of compound of Formula III was dissolved in N,N-Dimethylformamide (210 ml) at 25-35° C. Cesium carbonate (74.5 gr) and R-Tosyl tetrahydrofuran (26.8 gr) was added. Raised the temperature of the reaction mass to 45° C. to 50° C. and maintained for 12-24 hrs. Water and dichloromethane (525 ml) were added to the reaction mass and adjust the pH of the reaction mass to 7.0 to 8.0 using 5% hydrochloric acid solution. Separate the layers and extract the aqueous layer with dichloromethane. Organic layers were combined and washed with water, 10% sodium chloride, and dried over sodium sulphate. Filtered the solid and dried over vacuum to obtain empagliflozin as a residue.

Example 7: Preparation of Empagliflozin

The residue of compound of Formula III was dissolved in dimethylsulphoxide (210 ml) at 25-35° C. Cesium carbonate (74.5 gr) and R-Tosyl tetrahydrofuran (26.8 gr) was added. Raised the temperature of the reaction mass to 45° C. to 50° C. and maintained for 12-24 hrs. Water and 2-methyl tetrahydrofuran or dichloromethane were added and separate the layers and extract the aqueous layer with 2-methyl tetrahydrofuran or dichloromethane. Organic layers were combined and washed with sodium carbonate solution and dried over sodium sulphate. Filtered the solid and dried over vacuum to obtain empagliflozin as a residue Example 7: Preparation of Empagliflozin-DL-Pipecolic Acid The residue of empagliflozin, obtained according to Example 5 was added to DL-pipecolic acid (24 gr) and water (21 mL) at 80-85° C. and stirred the reaction mass for about 1 hr at 80-85° C. The reaction mass was allowed to cool to 25-35° C. and stirred for 24-48 hrs. Filtered the reaction mass and washed with n-butanol and dried the product at 45-50° C. under vacuum for 6-8 hrs.
Yield: 50 gms. HPLC: NLT 99.0%

Example 8: Preparation of Empagliflozin

Empagliflozin DL-Pipecolic acid co-crystal (100 gr) and dichloromethane (5000 ml) were taken in a round bottom flask at 25-35° C. pH of the reaction mass was adjusted to 7 to 8 using 10% Sodium carbonate solution. The reaction mass was maintained with stirring for 30-60 min. Layers were separated and the aqueous layer was extracted with dichloromethane (5000 ml). Combined organic layers and washed with 10% sodium chloride solution and dried over sodium sulphate. The reaction mass was filtered and washed with dichloromethane. Distilled off the solvent completely under vacuum to obtain pure Empagliflozin of formula I, as a residue.

Example 9: Preparation of Amorphous Empagliflozin

Methanol (105 ml) and dichloromethane (875 ml) were added to the residue of empagliflozin of formula I, obtained according to Example 8. The reaction mass temperature was raised to 45° C. and stirred further for 60-90 min. Filtered the reaction mass through 0.2 micron and feed the reaction mass through Spray dry instrument and dried the compound at 35-40° C. under vacuum for 10-12 hrs.

Yield: 28 gms

PXRD of amorphous empagliflozin is shown in FIG. 04.

Purity by HPLC: NLT: 99.0%

Example 10: Preparation of Crystalline Empagliflozin

Empagliflozin (10 gms) was dissolved in acetonitrile (150 ml) at reflux temperature, and stirred for 1-2 hrs. The reaction mass was slowly cooled to 25-35° C. and stirred for 2-3 hrs at 25-35° C. and filter the product dry at 40-45° C.

Dry wt: 7.0 gr

Purity by HPLC: 99.63%

Example 11: Preparation of Crystalline Empagliflozin

Empagliflozin (50 gms) was dissolved in n-butanol (250 ml) at reflux temperature, and stirred for 1-2 hrs. The reaction mass was slowly cooled to 25-35° C. and stirred for 2-4 hrs at 25-35° C. and filter the product, washed with n-butanol (100 ml) and dried at 75-85° C. The dried compound was added to n-butanol (250 ml) at reflux temperature, and stirred for 1-2 hrs. The reaction mass was slowly cooled to 25-35° C. and stirred for 2-4 hrs at 25-35° C. and filter the product, washed with n-butanol (100 ml) and dried at 75-85° C.

Dry wt: 20-35 gr

Purity by HPLC: 99%

Example 12: Purification of R-Tosyl Tetrahydrofuran

Crude R-Tosyl tetrahydrofuran (10 gms) was dissolved in ethyl acetate (40 ml) at 40-45° C. and cooled the reaction mass to 25-35° C. and further cool to −40 to −45° C. Reaction mass was maintained with stirring for 2-3 hrs at −40 to −45° C., filtered, washed with Ethyl acetate (Chilled −40° C.) and dried under vacuum at 25-35° C.

Yield: 6.0 gms

We claim:

1. A process for the preparation of empagliflozin of Formula I,

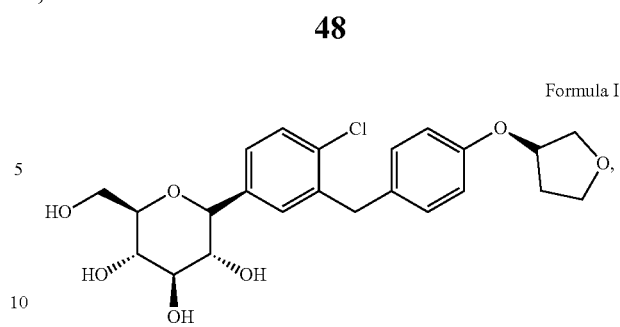

Formula I comprising:
a) reacting an aldehyde compound of Formula IX with a compound of Formula VIII, to obtain a compound of formula VII,

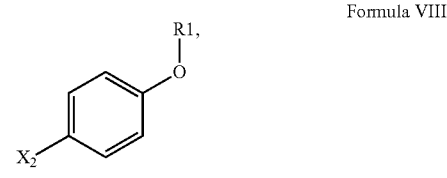

Formula VIII

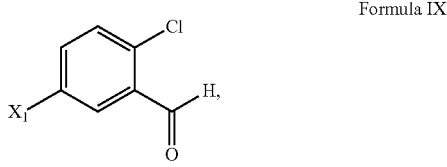

Formula IX

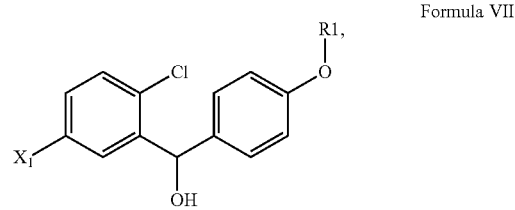

Formula VII wherein "$X_1$" and "$X_2$" independently represents a leaving group and $R_1$ represents hydrogen or a hydroxyl protecting group;

b) optionally protecting the hydroxyl group of the compound of Formula VII to obtain a compound of Formula VI,

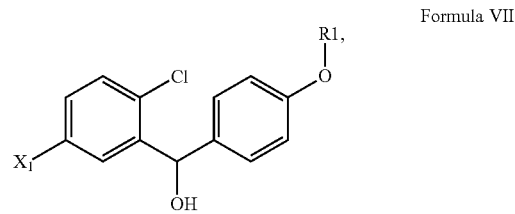

Formula VII

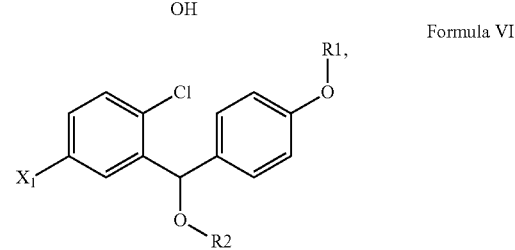

Formula VI wherein R₁ and R₂ independently represents hydrogen or a hydroxyl protecting group;

c) condensing the compound of Formula VII or its protected derivative of Formula VI with glucono lactone of the compound of Formula V to obtain a compound of formula IV",

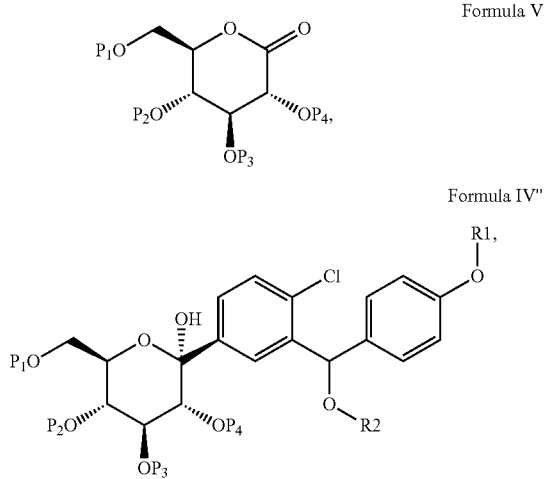

Formula V

Formula IV"

wherein R₁, R₂, P₁, P₂, P₃, and P₄ independently represents hydrogen or a hydroxyl protecting group;

d) converting the compound of Formula IV" to a compound of Formula IV,

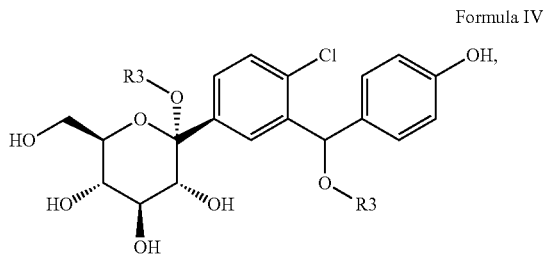

Formula IV wherein R₃ represents an alkyl group;

e) reducing the compound of Formula IV to a compound of Formula III,

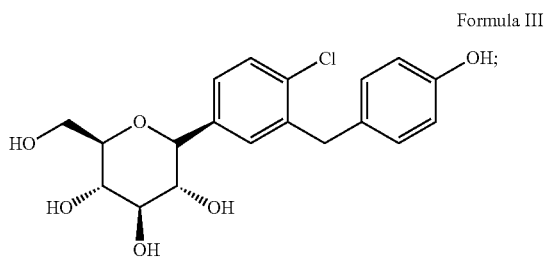

Formula III and f) reacting the compound of Formula III with a compound of Formula II to obtain the empagliflozin of Formula I,

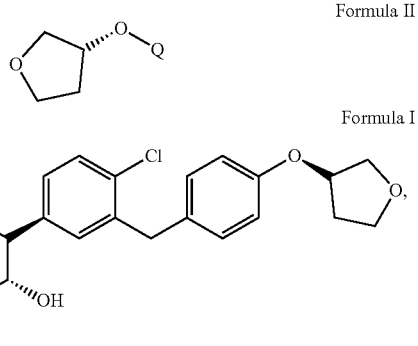

Formula II

Formula I wherein "Q" represents a leaving group.

2. The process as claimed in claim 1, wherein the "X₁" and "X₂" independently represents a leaving group selected from one of a halogen, methanesulfonyloxy, p-toluenesulfonyloxy, and pefluoroalkyl sulfonate;

wherein the R₁ and R₂ independently represents a hydroxyl protecting group selected from the group consisting of alkyl, acetyl, pivaloyl, methoxymethyl, benzyl, benzoyl, tert-butoxycarbonyl, benzyloxycarbonyl, tetrahydropyranyl, trimethylsilyl (TMS), triethylsilyl (TES), t-butyl(dimethyl)silyl (TBS), t-butyl(diphenyl)silyl (TBDPS), tri(isopropyl)silyl (TIPS), 2-(trimethylsilyloxy)ethyl, tert-Butyl 2,2,2-trichloroacetimidate, 4-Methoxybenzyl-2,2,2-trichloroacetimidate, Benzyl 2,2,2-trichloroacetimidate, methyl 2,2,2-trichloroacetimidate and O-allyl 2,2,2-trichloroacetimidate;

wherein the "P₁", "P₂", "P₃" and "P₄" independently represents a hydroxyl protecting group selected from the group consisting of alkyl, allyl, pivaloyl, acetyl (Ac), tosyl (Ts), mesyl (Ms), trimethylsilyl (TMS), tertiary butyldimethylsilyl (TBS), benzyl (Bn), paramethoxybenzyl (PMB), trityl (Tr), para-bromobenzoyl, para-nitrobenzoyl, benzoyl (Bz), triethylsilyl (TES), triisopropylsilyl (TIPS), benzyloxymethyl (BOM), p-methoxybenzyloxymethyl (PMBM), [(3,4-dimethoxybenzyl)oxy]methyl (DMBM), methoxymethyl (MOM), 2-methoxyethoxymethyl (MEM), methylthiomethyl (MTM), 2-(trimethylsilyl) ethoxymethyl (SEM).

3. The process as claimed in claim 2, wherein the "X₁" and "X₂" independently represents bromo, "R₁" represents tertiary butyldimethylsilyl (TBS), "R₂" represents trimethylsilyl group (TMS), and "P₁", "P₂", "P₃" and "P₄" independently represents trimethylsilyl group (TMS).

4. The process as claimed in claim 1, wherein the step a) is carried out with an organo lithium compound in an organic solvent.

5. The process as claimed in claim 4, wherein the organic solvent is selected from the group consisting of ethers selected from tetrahydrofuran, dimethyl ether, diisopropyl ether, and methyl tertiary butyl ether; aromatic hydrocarbons selected from toluene, and xylene; cyclic hydrocarbons selected from n-hexane, n-heptane, and cyclohexane; and halogenated hydrocarbons selected from methylene chloride, ethylene chloride, and chloroform.

6. The process as claimed in claim 4, wherein the organo lithium compound is n-butyl lithium and the organic solvent is tetrahydrofuran.

7. The process as claimed in claim 1, further comprises: isolating the compound of Formula VII using a water immiscible organic solvent.

8. The process as claimed in claim 1, wherein the compound of Formula VII exhibits less than 0.1% of each or all of des bromo impurity of Formula A, bromo phenol impurity of Formula B, keto impurity of Formula C, and dimer impurity of Formula D, as measured by HPLC,

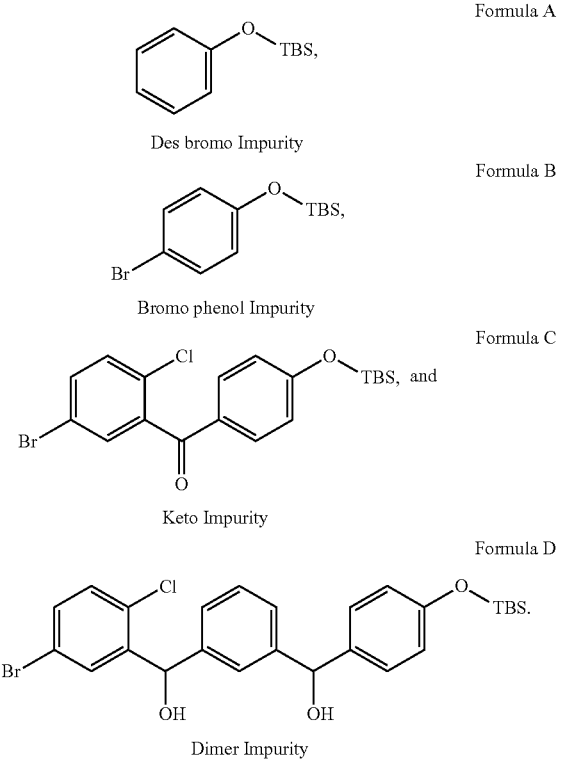

9. The process as claimed in claim 1, wherein the step c) is carried out with a organolithium compound in an organic solvent at a temperature of −10 and −90° C.

10. The process as claimed in claim 1, wherein the step d) comprises:
i) reacting the compound of Formula IV″ with an acid to obtain a compound of Formula IV 1

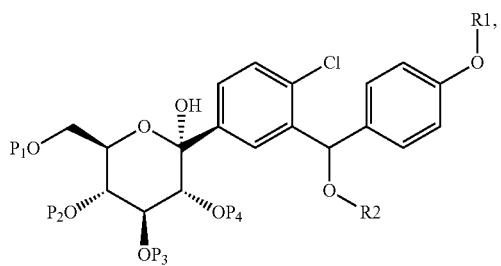

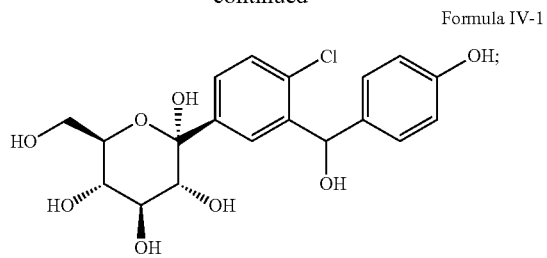

and
ii) treating the compound of Formula IV-1 simultaneously with an alcohol to obtain a compound of Formula IV,

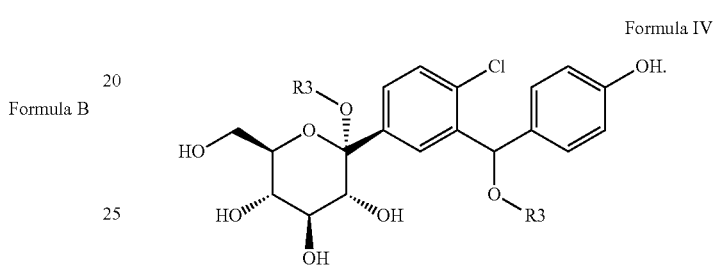

11. The process as claimed in claim 10, wherein the alkyl group is selected from the group consisting of methyl, ethyl, isopropyl and 2-methoxy ethyl.

12. The process as claimed in claim 10, wherein the acid is selected from the group consisting of an organic acid selected from formic acid, acetic acid, trifluoroacetic acid, methanesulfonic acid, oxalic acid and p-toluene sulfonic acid; an inorganic acid selected from hydrochloric acid, sulfuric acid and nitric acid; and a Lewis acid selected from boron trifluoride diethyletherate, scandium (III) trifluoromethanesulfonate, titanium (IV) isopropoxide, tin (IV) chloride, zinc (II) bromide, and zinc (II) chloride.

13. The process as claimed in claim 10, wherein the alcohol is selected from the group consisting of methanol, ethanol, isopropanol and 2-methoxy ethanol.

14. The process as claimed in claim 10, wherein the step d) further comprises isolating the compound of Formula IV using a solvent selected from the group consisting of 2-Methyl THF, ethyl acetate, n-heptane, and cyclohexane.

15. The process as claimed in claim 1, wherein the step e) is carried out using a reducing agent in the presence of a Lewis or a Bronsted acid in an organic solvent.

16. The process as claimed in claim 15, where in the reducing agent is selected from one of the group consisting of silane triethyl, tripropyl, triisopropyl, diphenylsilane, sodium borohydride, sodium cyanoborohydride, zinc borohydride, lithium aluminium hydride, diisobutylaluminum hydride, and samarium iodide; and
wherein the Bronsted acid is selected from the group consisting of hydrochloric acid, toluenesulphonic acid, trifluoroacetic acid, and acetic acid; and
wherein the Lewis acid is selected from the group consisting of boron trifluoride etherate, trimethylsilyltriflate, titanium tetrachloride, tin tetrachloride, scandium triflate, and zinc iodide.

17. The process as claimed in claim 15, wherein the organic solvent is selected from acetonitrile, methylene chloride and mixtures thereof.

18. The process as claimed in claim 15, wherein the step e) further comprises isolating the compound of Formula III using a solvent selected from the group selected from 2-Methyl THF, ethyl acetate, n-heptane, cyclohexane, and mixtures thereof.

19. The process as claimed in claim 1, wherein the leaving group in step f) is selected from the group consisting of a halogen selected from chloro, bromo or iodo; methanesulfonyloxy, p-toluenesulfonyloxy, and pefluoroalkyl sulfonate.

20. The process as claimed in claim 19, wherein the leaving group is p-toluenesulfonyloxy group.

21. The process as claimed in claim 1, wherein the step f) is carried out using a base in an organic solvent.

22. The process as claimed in claim 21, wherein the base is selected from the group consisting of sodium carbonate, potassium carbonate, caesium carbonate, sodium bicarbonate, potassium bicarbonate, sodium hydride, potassium ter-butoxide, ammonia, ammonium hydroxide, triethylamine, isopropyl ethylamine, diisopropyl amine, diisopropyl ethylamine, N-methyl morpholine, and piperidine; and
wherein the organic solvent is selected from the group consisting of methylene chloride, acetonitrile, dimethylsulfoxide, diethyl sulfoxide, dimethyl formamide, dimethyl acetamide, and N-methyl pyrrolidinone.

23. The process as claimed in claim 22, wherein the base is cesium carbonate and the organic solvent is dimethyl sulfoxide.

24. The process as claimed in claim 21, wherein the step f) further comprises isolating the empagliflozin using a solvent selected from the group consisting of 2-Methyl THF, ethyl acetate, n-heptane, and cyclohexane.

25. The process as claimed in claim 1, further comprises:
g) crystallizing the empagliflozin of Formula I using a solvent selected from the group consisting of methanol, ethanol, n-butanol, acetonitrile, dichloromethane and mixture thereof with water.

26. A process for the preparation of empagliflozin of Formula I,

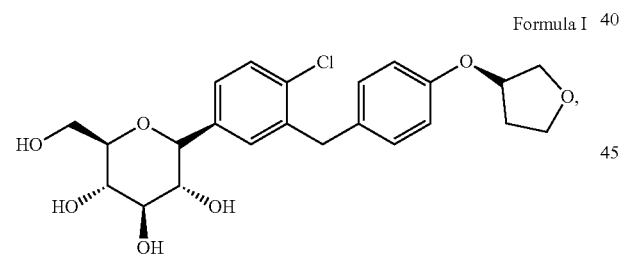

Formula I comprising:
a) reacting the compound of Formula VII or Formula VI with glucono lactone of compound of Formula V to obtain a compound of Formula IV'''; wherein $R_1$, $R_2$, $P_1$, $P_2$, $P_3$, and $P_4$ independently represents hydrogen or a hydroxyl protecting group,

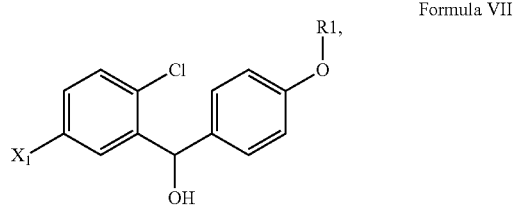

Formula VII

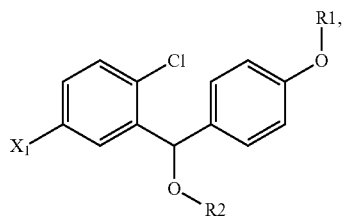

Formula VI

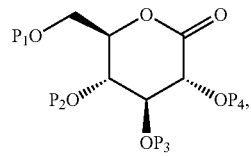

Formula V

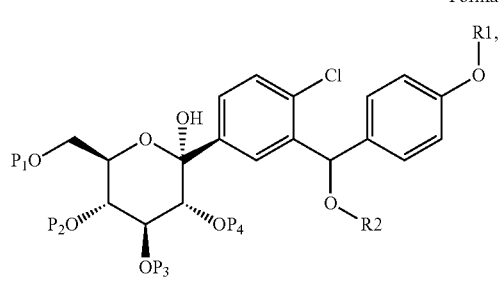

Formula IV'' b) converting the compound of Formula IV'' to a compound of Formula IV,

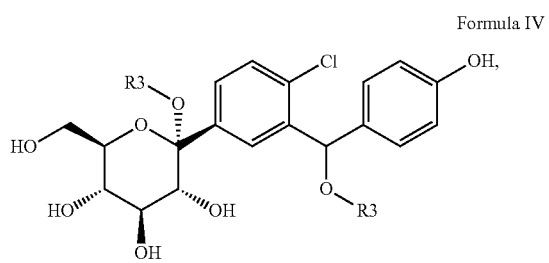

Formula IV wherein $R_3$ represents an alkyl group; and
c) converting the compound of Formula IV into the empagliflozin of Formula I.

27. The process as claimed in claim 26, wherein the step a) is carried out with a organolithium compound in an organic solvent at a temperature of −10 and −90° C.

28. The process as claimed in claim 26, wherein the organolithium compound is n-butyl lithium and the organic solvent is selected from the group consisting of toluene, and tetrahydrofuran.

29. The process as claimed in claim 26, wherein the step b) is carried out using an acid and an alcohol.

30. The process as claimed in claim 29, wherein the acid is methane sulfonic acid or hydrochloric acid and wherein the alcohol is selected from the group consisting of methanol, ethanol, isopropanol and 2-methoxy ethanol.

31. The process as claimed in claim 26, wherein the step c) is carried out using a reducing agent in the presence of Lewis or Bronsted acid in an organic solvent.

32. The process as claimed in claim 31, wherein the step c) is carried out using triethylsilane and boronon trifluoride diethyl etherate.

33. A process for the preparation of empagliflozin of Formula I,

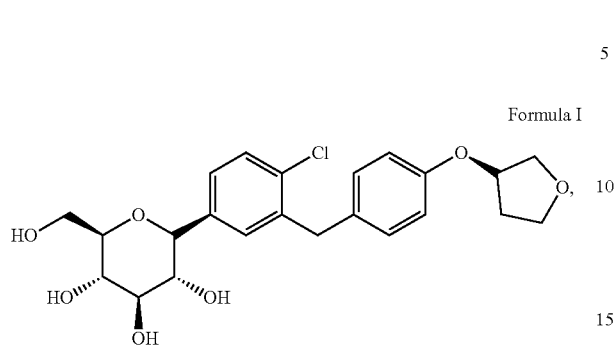

Formula I comprising:
a) reacting a compound of Formula IV" with a acid in an alcohol to obtain a compound of Formula IV,

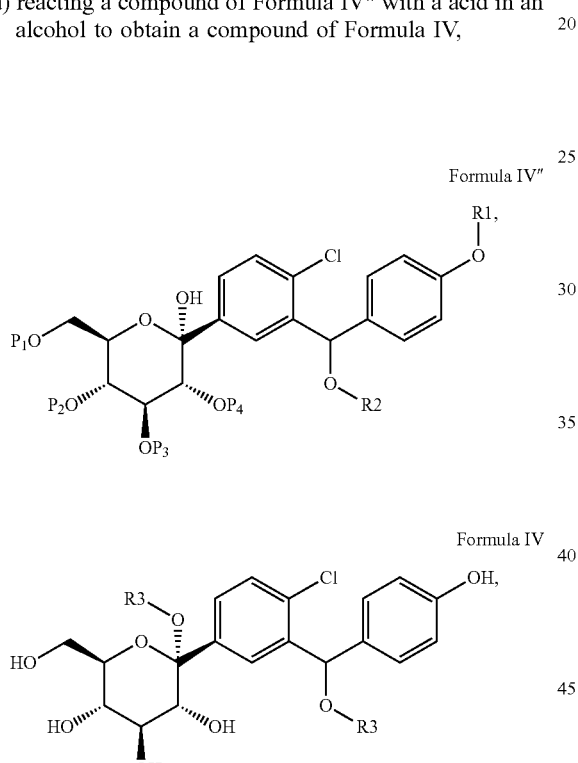

Formula IV"

Formula IV wherein $R_1$, $R_2$, $P_1$, $P_2$, $P_3$, and $P_4$ independently represents hydrogen or a hydroxyl protecting group, and wherein $R_3$ represents an alkyl group; and
b) converting the compound of Formula IV into the empagliflozin of Formula I.

34. The process as claimed in claim 33, wherein the acid is methane sulfonic acid or hydrochloric acid and wherein the alcohol is selected from the group consisting of methanol, ethanol, isopropanol and 2-methoxy ethanol.

35. The process as claimed in claim 33, wherein the step b) is carried out using a reducing agent in the presence of a Lewis or a Bronsted acid in an organic solvent.

36. The process as claimed in claim 35, wherein the step b) is carried out using triethylsilane and boronon trifluoride diethyl etherate.

37. A process for the preparation of empagliflozin of Formula I,

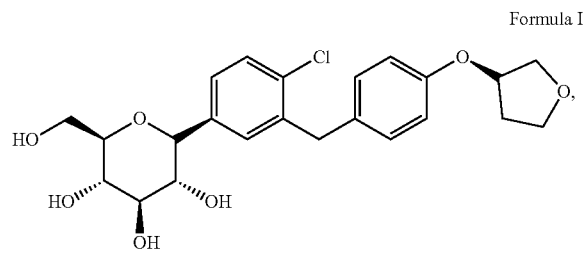

Formula I comprising:
a) reacting a compound of Formula IV with a reducing agent in presence of Bronsted acid in an organic solvent to obtain a compound of Formula III,

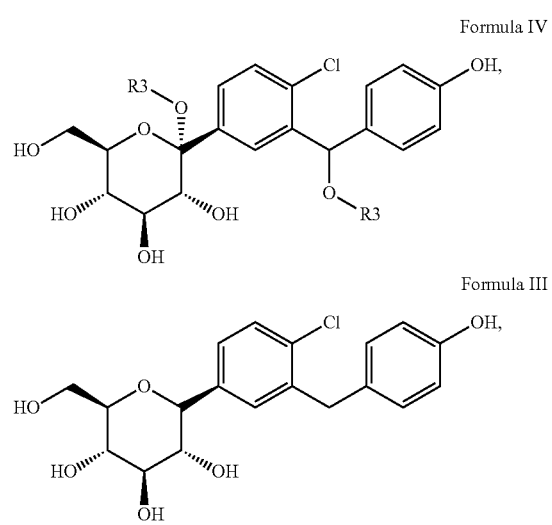

Formula IV

Formula III wherein $R_3$ represents an alkyl group; and
b) converting the compound of Formula III into the empagliflozin of Formula I.

38. The process as claimed in claim 37, wherein the reducing agent is triethylsilane and the Bronsted acid is boronon trifluoride diethyl etherate.

39. A process for the preparation of empagliflozin of Formula I,

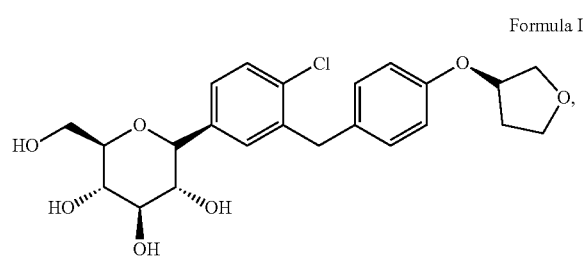

Formula I comprising:
a) reacting an aldehyde compound of Formula IX with a compound of Formula VIII, to obtain a compound of formula VII,

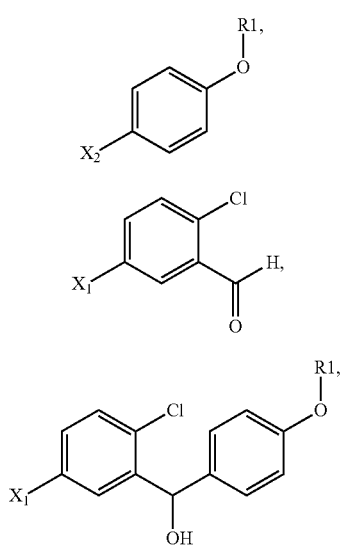

Formula VIII

Formula IX

Formula VII wherein "X₁", "X₂" independently represents a leaving group and R₁ represents hydrogen or a hydroxyl protecting group;

b) optionally protecting the hydroxyl group of the compound of Formula VII to obtain a compound of Formula VI,

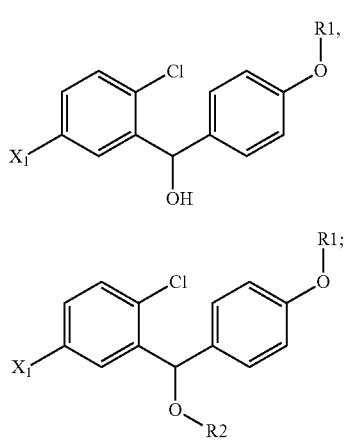

Formula VII

Formula VI and c) converting the compound of Formula VII or Formula VI into the empagliflozin of Formula I.

40. The process as claimed in claim 39, wherein the step a) is carried out with a organo lithium compound in an organic solvent.

41. The process as claimed in claim 40, wherein the organic solvent is selected from the group consisting of ethers selected from tetrahydrofuran, dimethyl ether, diisopropyl ether, and methyl tertiary butyl ether; aromatic hydrocarbons selected from toluene, and xylene; cyclic hydrocarbons selected from n-hexane, n-heptane, and cyclohexane; and halogenated hydrocarbons selected from methylene chloride, ethylene chloride, and chloroform.

42. The process as claimed in claim 40, wherein the organo lithium compound is n-butyl lithium and the organic solvent is tetrahydrofuran.

43. The process as claimed in claim 26, further comprising:

a) providing a solution of the empagliflozin of Formula I obtained in step (c), in one or more organic solvents, b) cooling the solution to produce precipitation of a crystalline empagliflozin; and c) isolating the crystalline empagliflozin.

44. The process as claimed in claim 43, wherein the one or more organic solvents are selected from one or more of the group consisting of methanol, ethanol, n-butanol, acetonitrile, dichloromethane, and water.

45. The process as claimed in claim 43, wherein the one or more organic solvents is n-butanol.

46. The process as claimed in claim 43, wherein the step a) is carried out at a temperature of about 30° C. to about reflux temperature.

47. The process as claimed in claim 26, wherein the empagliflozin of Formula I exhibits a chemical purity of about 99%, as measured by HPLC and contains less than 0.5% of total impurities.

48. The process as claimed in claim 26, wherein the empagliflozin of Formula I exhibits less than 0.1% as measured by HPLC of Impurity 5 or Impurity 6,

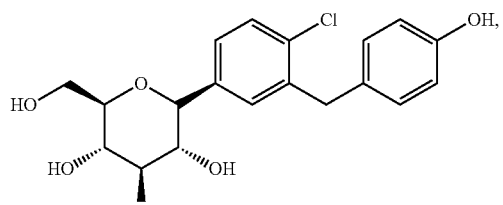

Desmethoxy Impurity 5

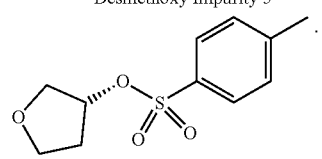

(R)-3-tosyl tetrahydrofuran of Formula IIA
Impurity 6

49. The process as claimed in claim 26, further comprising:

(d) forming a pharmaceutical composition comprising the empagliflozin of Formula I and at least one pharmaceutically acceptable excipient.

* * * * *